United States Patent
Tikoo et al.

(10) Patent No.: US 6,458,586 B1
(45) Date of Patent: Oct. 1, 2002

(54) BOVINE CELLS EXPRESSING ADENOVIRUS ESSENTIAL FUNCTIONS FOR PROPAGATION OF RECOMBINANT ADENOVIRAL VECTORS

(75) Inventors: Suresh Kumar Tikoo; Lorne A. Babiuk, both of Saskatoon (CA); Police Seshidhar Reddy, Gaithersburg, MD (US)

(73) Assignee: University of Saskatchewan, Saskatoon (CA)

(*) Notice: Subject to any disclaimer, the term of this patent is extended or adjusted under 35 U.S.C. 154(b) by 0 days.

(21) Appl. No.: 09/423,156

(22) PCT Filed: Nov. 1, 1999

(86) PCT No.: PCT/US99/25677

§ 371 (c)(1),
(2), (4) Date: Nov. 1, 1999

(87) PCT Pub. No.: WO00/26395

PCT Pub. Date: May 11, 2000

Related U.S. Application Data

(60) Provisional application No. 60/155,219, filed on Nov. 2, 1998.

(51) Int. Cl.[7] .......................... C12N 5/06; C12N 7/01; C12N 15/86; C12N 15/861; A61K 39/235
(52) U.S. Cl. ................. 435/325; 435/320.1; 435/235.1; 424/233.1; 424/199.1; 424/93.1; 424/93.2; 424/813; 536/23.1; 536/23.72
(58) Field of Search .............................. 435/325, 320.1, 435/235.1; 424/93.1, 93.21, 199.1, 233.1, 813; 536/23.1, 23.72

(56) References Cited

U.S. PATENT DOCUMENTS

| | | | |
|---|---|---|---|
| 5,820,868 A | * 10/1998 | Mittal et al. ............. | 424/199.1 |
| 5,981,258 A | 11/1999 | Mehtali et al. | |
| 6,127,175 A | 10/2000 | Vigne et al. | |

FOREIGN PATENT DOCUMENTS

| | | |
|---|---|---|
| EP | 0 259 149 A2 | 3/1988 |
| WO | WO 95/16048 A2 | 6/1995 |
| WO | WO 95/16780 A1 | 6/1995 |
| WO | WO 96/22378 A1 | 7/1996 |
| WO | WO 98/59063 A2 | 12/1998 |

OTHER PUBLICATIONS

Zheng et al., 1994, Virus Research vol. 31, pp. 163–186.*
Fallaux et al., 1996, Human Gene Therapy vol. 7, pp. 215–222.*
Zakhartchouk et al., Oct. 1998, Virology Vo. 250, pp. 220–229.*
Verma et al. 1997, Nature vol. 389, pp. 239–242.*
Adra, C.N. et al. (1987). "Cloning and Expression of the Mouse pgk–1 Gene and the Nucleotide Sequence of its Promoter," *Gene* 60:65–74.

Amalfitano, A. et al. (1996). "Improved Adenovirus Packaging Cell Lines to Support the Growth of Replication–Defective Gene–Delivery Vectors," *PNAS USA* 93:3352–3356.
Ausubel, F.M. et al., eds. (1987). *Current Protocols In Molecular Biology.* vol. 1, John Wiley & Sons, Inc., pp. iii–xii (Table of Contents).
Brennan, S. and Savage, S. (1990). "Embryonic Transcriptional Activation of a Xenopus Cytoskeletal Actin Gene Does Not Require a Serum Response Element," *Roux's Arch. Dev. Biol.* 199:89–96.
Buchacher, A. et al. (1992). "Human Monoclonal Antibodies Against gp41 and gp120 as Potential Agent for Passive Immunization," *Vaccines92: Modern Approaches to New Vaccines Including Prevention of AIDS.* F. Brown et al., eds. Cold Spring Harbor Laboratory Press: New York. pp. 191–195.
Byrn, R.A. et al. (Apr. 12, 1990). "Biological Properties of a CD4 Immunoadhesin," *Nature* 344:667–670.
Capon, D.J. et al. (Feb. 9, 1989). "Designing CD4 Immunoadhesins for AIDS Therapy," *Nature* 337:525–531.
Chartier, C. et al. (1996). "Efficient Generation of Recombinant Adenovirus Vectors by Homologous Recombination in *Escherichia coli,*" *J. Virol.* 70(7):4805–4810.
Chroboczek, J. et al. (1992). "The Sequence of the Genome of Adenovirus Type 5 and its Comparison with the Genome of Adenovirus Type 2," *Virology* 186(1):280–285 (GenBank Accession No. M73260).
Deregt, D. et al. (1987). "Monoclonal Antibodies to Bovine Coronavirus: Characteristics and Topographical Mapping of Neutralizing Epitopes on the E2 and E3 Glycoproteins," *Virology* 161:410–420.
Deregt, D et al. (1989). "Monoclonal Antibodies to Bovine Coronavirus Glycoproteins E2 and E3: Demonstration of in vivo Virus–Neutralizing Activity," *J. Gen. Virol.* 70:993–998.
Fallaux, F.J. et al. (Sep. 1, 1998). "New Helper Cells and Matched Early Region 1–Deleted Adenovirus Vectors Prevent Generation of Replication–Competent Adenoviruses," *Hum. Gene Ther.* 9:1909–1917.
Freshney, R.I., ed. (1986). *Animal Cell Culture: A Practical Approach.* IRL Press:Oxford, pp. vii–xii (Table of Contents).
Gait, N., ed. (1984). *Oligonucleotide Synthesis: A Practical Approach.* IRL Press; Oxford, pp. vii–xii (Table of Contents).

(List continued on next page.)

Primary Examiner—Ali R. Salimi
Assistant Examiner—Baoqun Li
(74) *Attorney, Agent, or Firm*—Morrison & Foerster LLP

(57) ABSTRACT

The invention provides cell lines capable of supporting the replication of a defective recombinant virus vector. In one aspect, bovine cell lines expressing adenovirus E1 functions are provided. The cell lines are useful for the propagation of adenovirus vectors with mutations and/or deletions in E1 and other essential regions of the adenovirus genome.

33 Claims, 10 Drawing Sheets

OTHER PUBLICATIONS

Ginsberg, H.S. and Young, C.S.H. (1977). "Genetics of Adenoviruses," Chapter 2 In *Comprehensive Virology.* vol. 9, H. Fraenkel–Conrat et al., eds., Plenum Press: New York, pp. 27–88.

Glover, D.M., ed. (1985). *DNA Cloning: A Practical Approach.* vols. I, IRL Press:Oxford, pp. vii–xii (Table of Contents).

Glover, D.M., ed. (1985). *DNA Cloning: A Practical Approach.* vols. II, IRL Press:Oxford, pp. vii–xiv (Table of Contents).

Graham, F.L. et al. (1977). "Characteristics of a Human Cell Line Transformed by DNA From Human Adenovirus Type 5," *J. Gen. Virol.* 36:59–72.

Graham, F.L. and Prevec, L. (1991). "Manipulation of Adenovirus Vectors," Chapter 11 In *Methods in Molecular Biology.* vol. 7, E.J. Murray, ed., Humana Press: New Jersey, pp. 109–128.

Hames, B. and Higgins, S., eds. (1984). *Transcription and Translation: A Practical Approach.* IRL Press: Oxford, pp. vii–xii (Table of Contents).

Hames, B. and Higgins, S., eds. (1985). *Nucleic Acid Hybridization: A Practical Approach.* IRL Press: Oxford, pp. ix–xiv (Table of Contents).

Hehir, K.M. et al. (Dec. 1996). "Molecular Characterization of Replication–Competent Variants of Adenovirus Vectors and Genome Modifications to Prevent Their Occurrence," *J. Virol.* 70(12):8459–8467.

Hirt, B. (1967). "Selective Extraction of Polyoma DNA from Infected Mouse Cell Cultures," *J. Mol. Biol.* 26:365–369.

Hughes, G. et al. (1988). "Functional and Topographical Analyses of Epitopes on Bovine Herpesvirus Type 1 Glycoprotein IV," *Arch. Virol.* 103:47–60.

Imler, J. (1998). "Adenovirus Vectors as Recombinant Viral Vaccines," *Vaccine* 13:1143–1151.

Klessig, D.F. et al. (Jul., 1984). "Introduction, Stable Integration, and Controlled Expression of a Chimeric Adenovirus Gene Whose Product is Toxic to the Recipient Human Cell," *Mol. Cell. Biol.* 4(7):1354–1362.

Kunkel, T.A. et al. (1987). "Rapid and Efficient Site–Specific Mutagenesis Without Phenotypic Selection," *Meth. Enzymol.* 154:367–382.

Kurachi, K. et al. (1985). "Sequence of the cDNA and Gene for Angiogenin, a Human Angiogenesis Factor," *Biochem.* 24:5494–5499.

Lathe, R. et al. (1987). "Plasmid and Bacteriophage Vectors for Excision of Intact Inserts," *Gene* 57:193–201.

Maniatis, T. et al., eds. (1982). *Molecular Cloning: A Laboratory Manual: A Laboratory Manual.* Cold Spring Harbor Laboratory Press, pp. v–x (Table of Contents).

Perbal, B., ed. (1984). *A Practical Guide to Molecular Cloning.* John Wiley & Sons: New York, pp. xi–xix (Table of Contents).

Reddy, P.S. (1999). "Replication–Defective Bovine Adenovirus Type 3 as an Expression Vector," *J. Virol.* 73(11):9137–9144.

Sambrook, J. et al., eds. (1989). *Molecular Cloning: A Laboratory Manual.* $2^{nd}$ Edition; vols. I, II & III, Cold Spring Harbor Laboratory Press, pp. xi–xxxviii (Table of Contents).

Shenk, T. (1996). "Adenoviridae: The Viruses and Their Replication," Chapter 67 In *Virology.* $3^{rd}$ Edition, B. Fields et al., eds., Lippincott–Raven: Philadelphia, pp. 2111–2148.

Takemori, N. (1972). "Genetic Studies with Tumorigenic Adenoviruses: III. Recombination in Adenovirus Type 12," *Virology* 47:157–167.

Traunecker, A. et al. (Jan. 7, 1988). "Soluble CD4 Molecules Neutralize Human Immunodeficiency Virus Type 1," *Nature* 331:84–86.

Weinberg, D.H. and Ketner, G. (Sep. 1983). "A Cell Line That Supports the Growth of a Defective Early Region 4 Delection Mutant of Human Adenovirus Type 2," *PNAS USA* 80:5383–5386.

Williams J. et al. (Feb. 1975). "Adenovirus Recombination: Physical Mapping of Crossover Events," *Cell* 4:113–119.

Yeh, P. and Perricaudet, M. (Jul. 1997). "Advances in Adenoviral Vectors: From Genetic Engineering to their Biology," *FASEB J.* 11(8):615–623.

Zheng, B. et al. (1994). "The E1 Sequence of Bovine Adenovirus Type 3 and Complementation of Human Adenovirus Type 5 E1A Function in Bovine Cells," *Virus Res.* 31:163–186.

Zoller, M.J. and Smith, M. (1982). "Oligonucleotide–Directed Mutagenesis Using M13–Derived Vectors: An Efficient and General Procedure for the Production of Point Mutation in any Fragment of DNA," *Nucl. Acids Res.* 10(2):6487–6500.

* cited by examiner

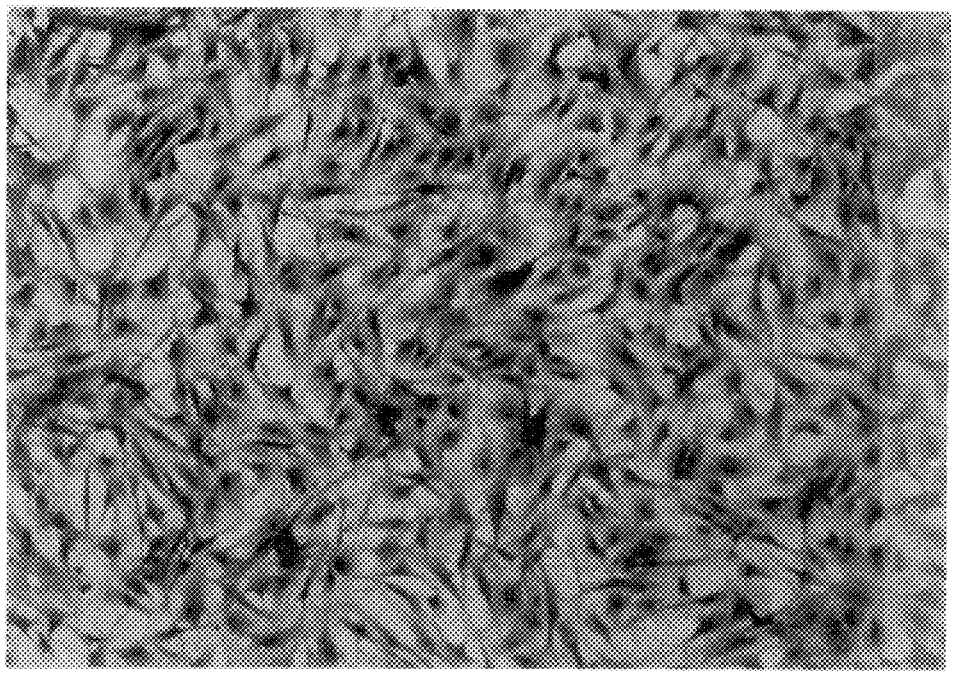
FIG._2A
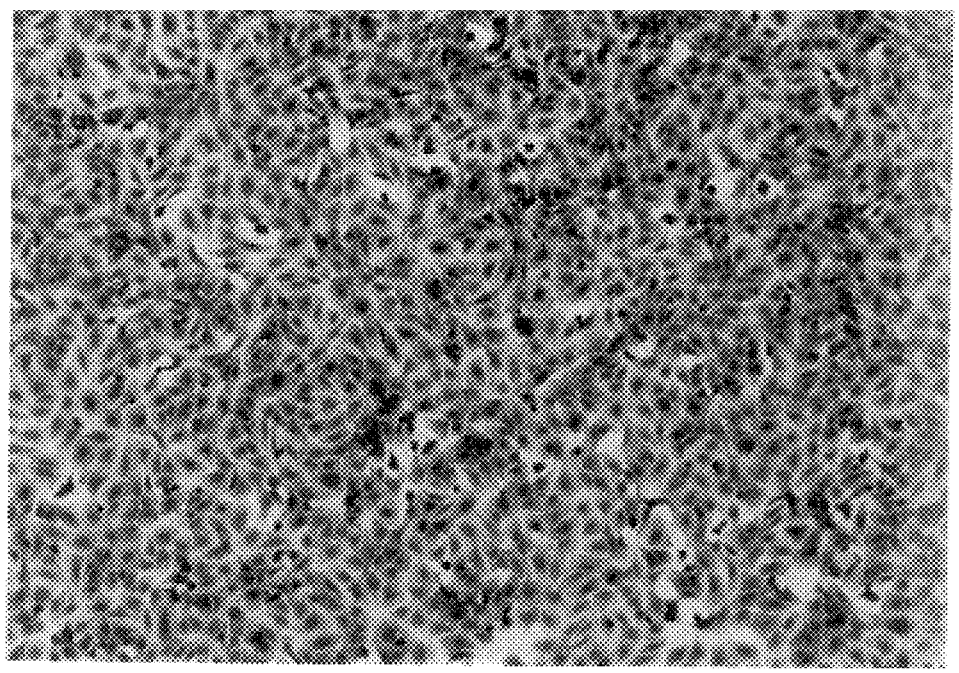
FIG._2B

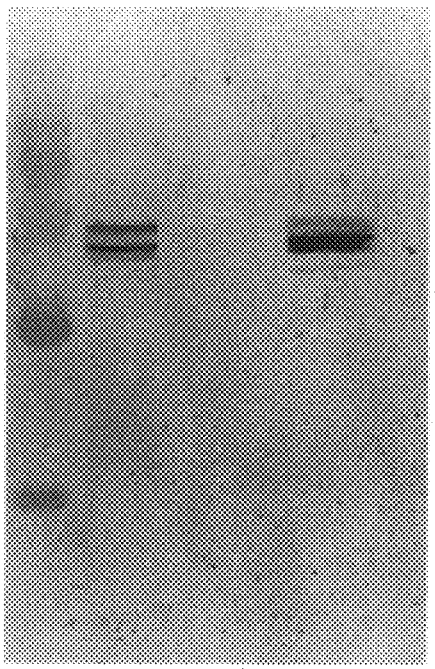 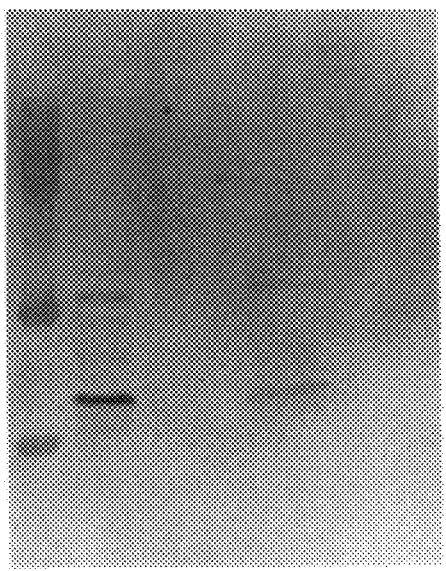
FIG._3          FIG._4

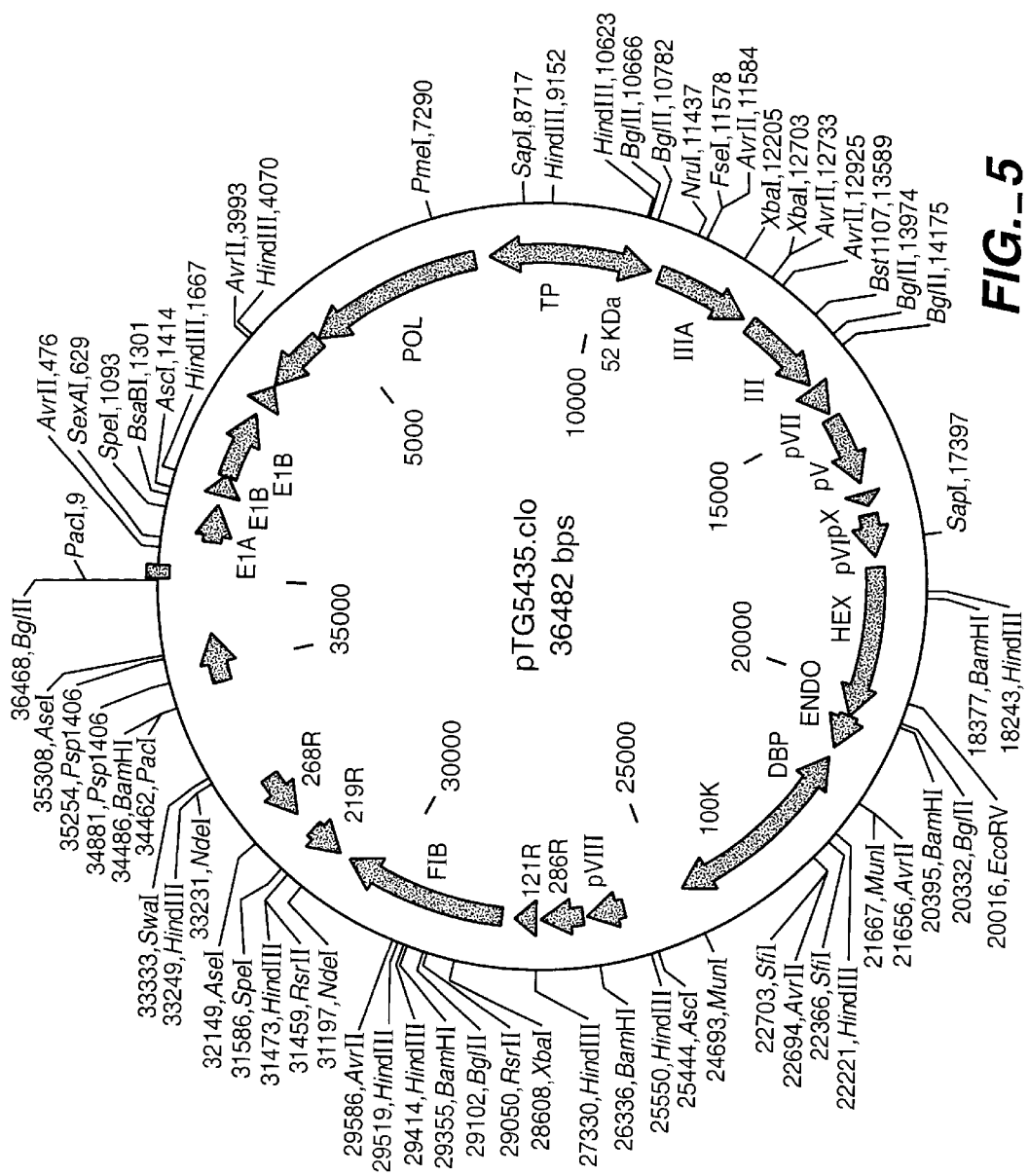
FIG._5

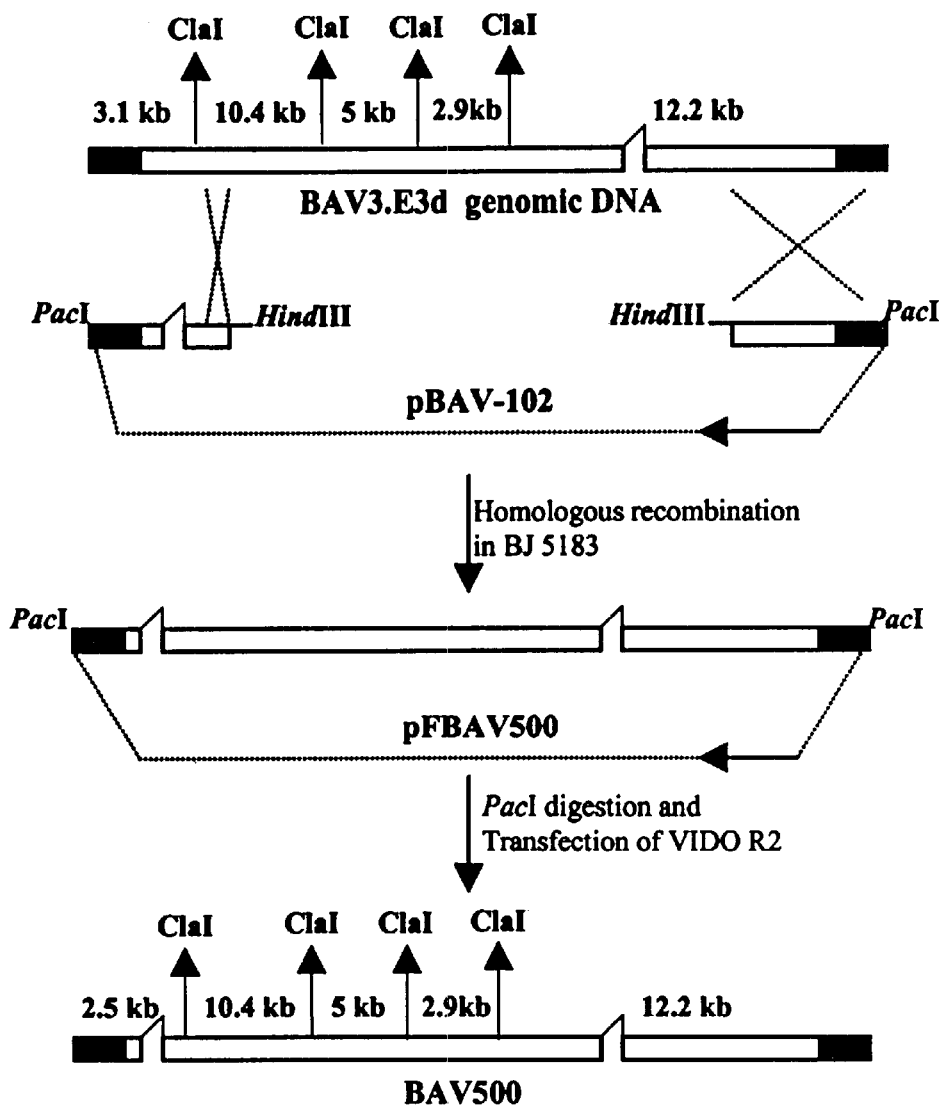
FIG._6

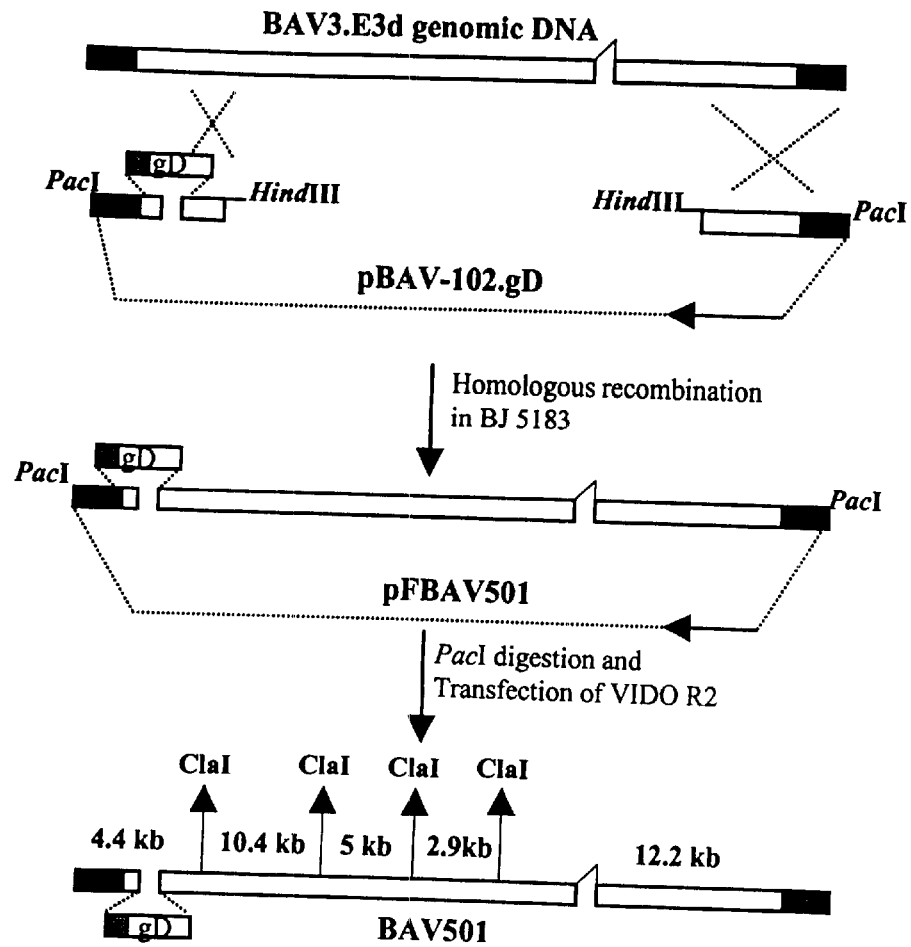
FIG._7

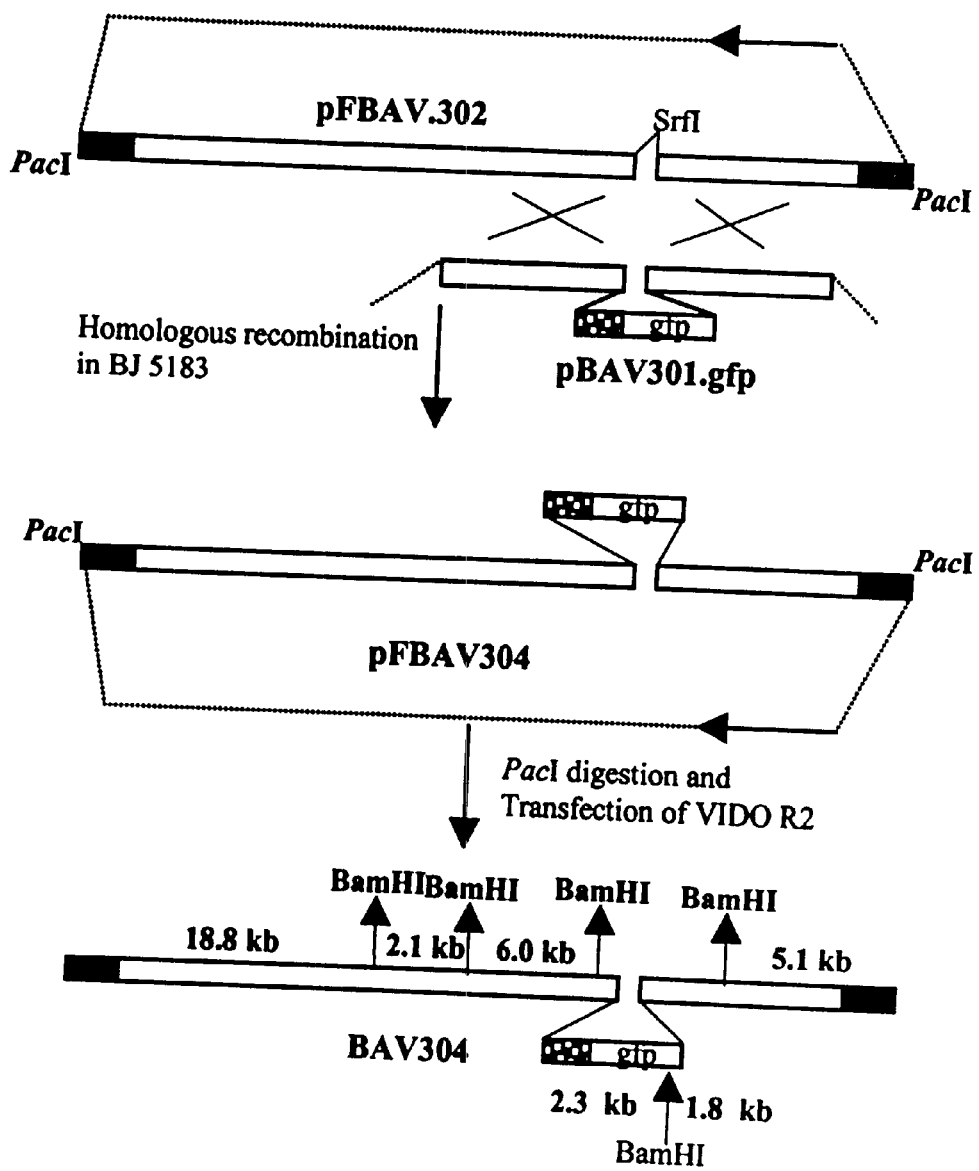
FIG._9

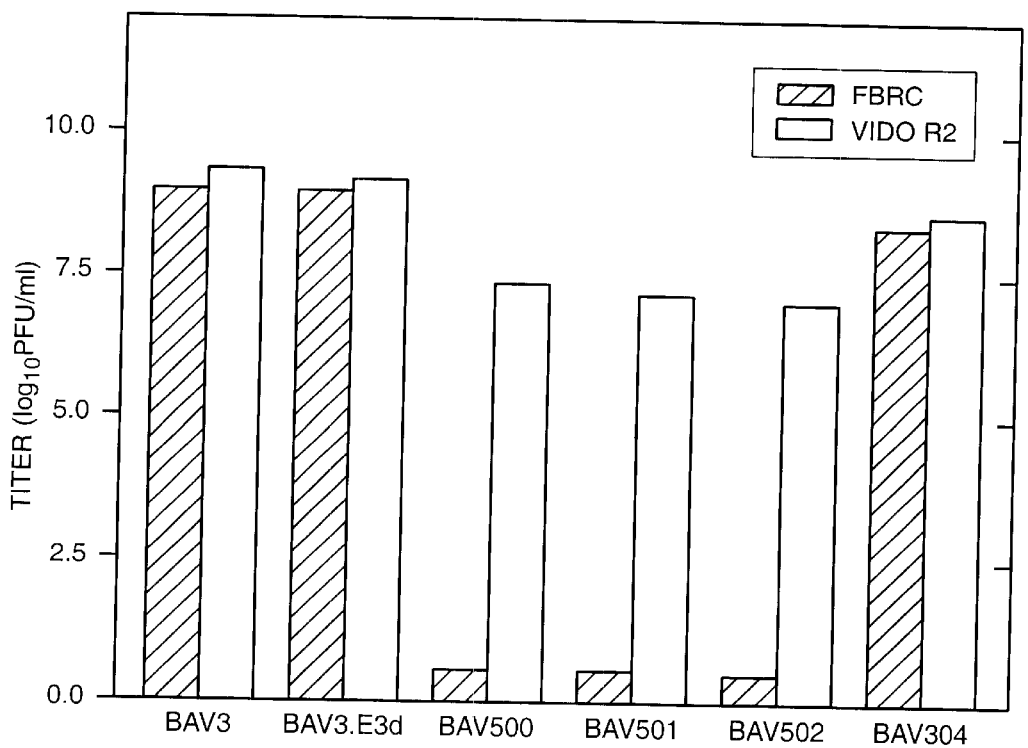
FIG._10

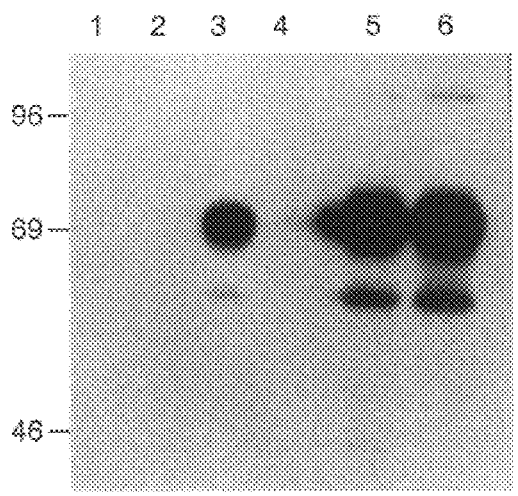
FIG._11A
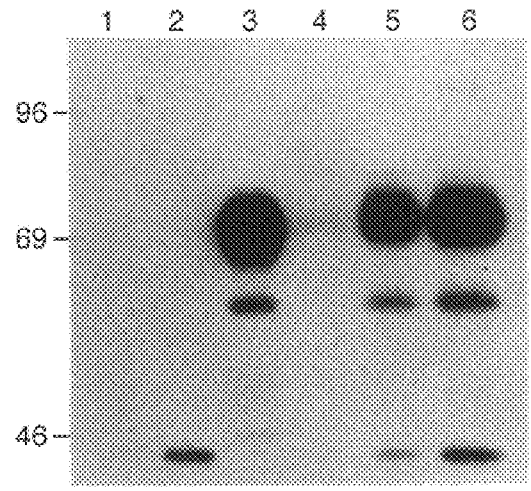
FIG._11B
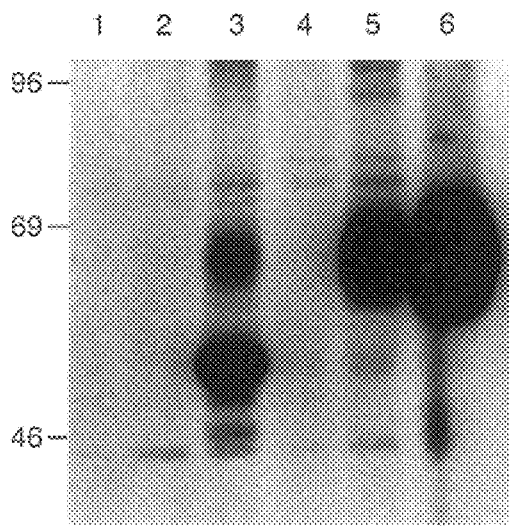
FIG._12
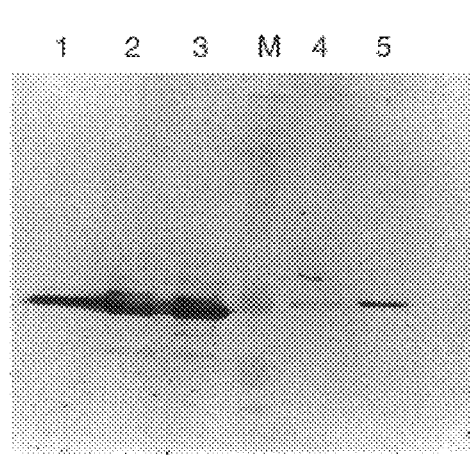
FIG._13

BOVINE CELLS EXPRESSING ADENOVIRUS ESSENTIAL FUNCTIONS FOR PROPAGATION OF RECOMBINANT ADENOVIRAL VECTORS

CROSS-REFERENCE TO RELATED APPLICATIONS

This application is a 371 of PCT/US99/25677 filed Nov. 1, 1999 which claims priority to U.S. provisional patent application Ser. No. 60/155,219, filed on Nov. 2, 1998.

TECHNICAL FIELD

The invention is in the fields of recombinant cell lines, recombinant animal viral vectors, defective adenovirus vectors, subunit vaccines and gene therapy.

BACKGROUND

Adenoviruses have recently begun to be used as vectors for gene expression, recombinant subunit vaccines and gene therapy. Yeh et al. (1997) *FASEB J.* 11:615–623; and Imler (1998) *Vaccine* 13:1143–1151. They have been detected in many animal species, exhibit minimal pathogenicity, and are non-integrative. Adenoviruses are capable of infecting a wide variety of cell types, both dividing and quiescent, and have a natural tropism for airway epithelial cells. The advantages to the use of adenoviruses as vectors include suitability for genetic manipulation, ability to replicate to high titers, stability and ease of production. Adenoviruses have been used as live enteric viral vaccines for many years with an excellent safety profile.

Adenoviruses are distinguished according to the species of animal which they infect (e.g., human, bovine, canine, etc.). Particular species of adenoviruses are further characterized serologically, according to type.

The adenovirus E1 region encodes several functions that are essential to viral replication. The E1A region is responsible for encoding functions that activate early and late transcription, stimulate progression of infected cells into the S phase of the cell cycle, and antagonize the effects of α- and β-interferons. The E1B region encodes functions involved in stimulating cell-cycle progression of infected cells, blocking apoptosis in infected cells, and blocking nucleocytoplasmic transport of host cell mRNA. In addition, part or all of the E1 region is responsible for cell transformation. See, for example, Shenk, Adenoviridae: The viruses and their replication. In "Virology" (B. Fields, ed.) Chapter 67, Lippincott-Raven, Philadelphia, 1996, pp. 2111–2148.

Ideally (for safety considerations), one or more essential regions of the adenovirus genome are inactivated in the genome of an adenoviral vector. For example, the E1 region, encoding several essential functions (see above) as well as potential adenovirus transforming functions, will be inactivated in many types of adenovirus vector. However, since the E1 regions are essential for normal virus replication, propagation of adenovirus vectors lacking all or part of the E1 regions requires a helper cell line that provides E1 functions. Heretofore, such helper cell lines have provided E1 function by including E1 sequences from the same adenovirus type that is propagated in the cell line. For example, the human 293 cell line, containing human adenovirus type 5 E1 sequences, can be used for the propagation of human adenovirus with a mutated E1 region. Graham et al. (1977) *J. Gen. Virol.* 36:59–72. Similarly, cell lines suitable for the propagation of E2- and E4-mutant adenoviruses have been described. Klessig et al. (1984) *Mol. Cell. Biol.* 4:1354–1362; Weinberg et al. (1983) *Proc. Natl. Acad. Sci. USA* 80:5383–5386.

Homologous recombination occurs readily between adenoviruses of the same type, both in the wild and during coinfection of cultured cells. Ginsberg et al. The Genetics of Adenoviruses. In: Fraenkel-Conrat H and Wagner R R eds., "Comprehensive Virology" volume 9, New York, Plenum Press, 1977; Takemori (1972) *Virology* 47:157–167; and Williams et al. (1975) *Cell* 4:113–119. Consequently, when a mutant adenovirus is passaged through a helper cell line containing homologous adenovirus sequences, homologous recombination can result in the generation of wild-type adenoviruses. For example, when replication-defective adenoviruses containing E1 deletions were passaged in a complementing cell line containing adenovirus E1 sequences, replication-competent viruses emerged, in which the deleted E1 region had been restored through recombination with homologous E1 sequences present in the helper cell. See, for example, Hehir et al. (1996) *J. Virol.* 70:8459–8467; Fallaux et al. (1998) *Human Gene Therapy* 9:1909–1917.

Accordingly, there is a need for an adenovirus vector-helper cell system in which vectors deleted for E1 can be propagated in a cell line providing E1 function, without the likelihood that wild-type virus will be generated by recombination between the vector genome and viral sequences in the helper cell.

SUMMARY OF THE INVENTION

It is an object of the invention to provide a system for the growth and propagation of replication-defective adenovirus vectors, wherein the system does not have the potential to produce recombinant, replication-competent adenoviruses.

Accordingly, the invention provides host cells, preferably bovine, that are permissive for the replication of a defective adenovirus vector, in particular, a recombinant adenovirus that is mutated in the E1 region of the adenovirus genome (i.e., the E1A region, the E1B region or both). The E1 mutation can be a deletion, insertion, substitution, one or more point mutation(s), a rearrangement, or any other type of in vivo or in vitro genetic change. Such defective adenovirus vectors will often comprise heterologous sequences. In adenovirus genomes with deletions in E1, the heterologous sequences can be inserted at or near the site formerly occupied by the deleted E1 sequences, and/or at any other region of the genome. Adenovirus genomes that are mutant in their E1 region can also contain mutations in other regions of the genome, such as the E3 region or the region between E4 and the right end of the genome.

In one embodiment, host cells comprise E1 sequences from an adenovirus of a different type or a different species than the adenovirus vector that is propagated in the host cells. In a preferred embodiment, the host cells comprise human adenovirus E1 sequences and the vector that is propagated in the host cells is a bovine adenovirus.

In one embodiment, the bovine host cells are derived from fetal bovine retina. In a preferred embodiment, fetal bovine retina cells comprise adenovirus E1 sequences that have been introduced into the cells by transfection. In a more preferred embodiment, the E1 sequences are derived from a human adenovirus, for example, human adenovirus type 5 (HAd-5). In a still more preferred embodiment, fetal bovine retina cells, comprising HAd-5 sequences are used for the propagation of replication-defective bovine adenovirus (BAV) vectors having one or more mutations in their E1 region and, optionally, one or more mutations in other regions of their genome. In an even more preferred embodiment, the replication-defective BAV vectors comprise heterologous sequences, wherein the heterologous sequences can be located in the E1 region of the genome of the defective BAV vector and/or at other regions of the genome.

The invention provides host cells as described above, as well as host cells comprising defective BAV vectors mutated in their E1 region, wherein the defective BAV vectors optionally comprise inserted heterologous sequences.

In addition, the invention provides methods for the propagation of replication-defective recombinant BAV vectors using the host cells of the invention, as well as vectors and vector genomes that have been propagated using the host cells of the invention. Defective recombinant BAV vectors and their genomes, produced using the methods and compositions of the invention, are useful as immunogenic compositions. Such immunogenic compositions can be used both prophylactically and therapeutically. Prophylactically, the immunogenic compositions are used for purposes of vaccination to elicit a protective immune response. In their therapeutic uses, the immunogenic compositions are used to induce or boost an immune response to an infection, thereby preventing or ameliorating the symptoms of disease.

In addition, defective recombinant BAV vectors and their genomes, produced using the methods and compositions of the invention, are useful for the introduction of heterologous genes into recipient mammalian cells. When such heterologous genes are in operative linkage with appropriate transcriptional regulatory elements, expression of the heterologous gene in the recipient cell is accomplished. Such expression is useful in the provision of therapeutic gene(s) and/or gene product(s) and thus will play a role in certain aspects of in vitro, in vivo and ex vivo genetic intervention in the treatment of disease, and in gene therapy.

BRIEF DESCRIPTION OF THE DRAWINGS

FIG. 2 contains micrographs showing cellular morphology. FIG. 2A shows fetal bovine retina cells (FBRC). FIG. 2B shows VIDO-R2 cells (FBRC transformed by pTG4671).

FIG. 3 shows analysis of E1A expression in FBRC and VIDO-R2 cells by protein immunoblot analysis. Human 293 cells, which express human adenovirus type 5 E1A and E1B, are used as a positive control. Lane 1: molecular weight markers; lane 2: 293 cells; lane 3: FBRC; lane 4: VIDO-R2 cells.

FIG. 4 shows analysis of E1B expression in FBRC and VIDO-R2 cells by protein immunoblot analysis. Human 293 cells, which express human adenovirus type 5 E1A and E1B, are used as a positive control. Lane 1: molecular weight markers; lane 2: 293 cells; lane 3: FBRC; lane 4: VIDO-R2 cells.

FIG. 5 shows a map of plasmid TG5435, comprising a BAV genome. BAV genes are designated by the thick arrows inside the circle.

FIG. 6 is a schematic diagram showing the construction of BAV3.500. See Example 4.

FIG. 7 is a schematic diagram showing the construction of BAV3.501. See Example 5.

FIG. 9 is a schematic diagram showing the construction of BAV3.304. See Example 7.

FIG. 10 shows titers of wild-type and recombinant BAVs after infection of FBRC and VIDO R2 cells. See Example 8.

FIG. 11 shows expression of BHV gD in BAV3.501-infected cells. See Example 9. $^{35}$S labeled proteins from cell lysates were immunoprecipitated with anti-gD monoclonal antibodies and separated under reducing conditions on a 10% polyacrylamide-SDS gel. FIG. 11A shows results in VIDO R2 cells; FIG. 11B shows results in MDBK cells. Lane 1: mock-infected; Lane 2: BAV3-infected; Lane 3: BHV-1-infected; Lanes 4–6: BAV3.501-infected and harvested at 12 hours (lane 4), 24 hours (lane 5) and 36 hours (lane 6) after infection. Molecular weight markers, in kDa, are indicated at the left side of the figure.

FIG. 12 shows expression of BCV HE in BAV3.502-infected VIDO R2 cells. See Example 10. $^{35}$S labeled proteins from cell lysates were immunoprecipitated with polyclonal anti-BCV serum and separated under reducing conditions on a 10% polyacrylamide-SDS gel. Lane 1: mock-infected; Lane 2: BAV3-infected; Lane 3: BCV-infected; Lanes 4–6: BAV3.502-infected and harvested at 12 hours (lane 4), 24 hours (lane 5) and 36 hours (lane 6) after infection. Molecular weight markers, in kDa, are indicated at the left side of the figure. Two different autoradiographic exposures of the gel are shown.

FIG. 13 shows expression of GFP in BAV3.304-infected MDBK cells. Infected cell lysates were separated by gel electrophoresis, and the gels were blotted and probed with anti-GFP serum. Lanes 1–3: BAV3.304-infected cells harvested as 12 (lane 1), 24 (lane 2) and 36 (lane 3) hours after infection; Lane 4: mock-infected; Lane 5: wild-type BAV-3-infected.

DETAILED DESCRIPTION

A. General Methods

Figure 1:
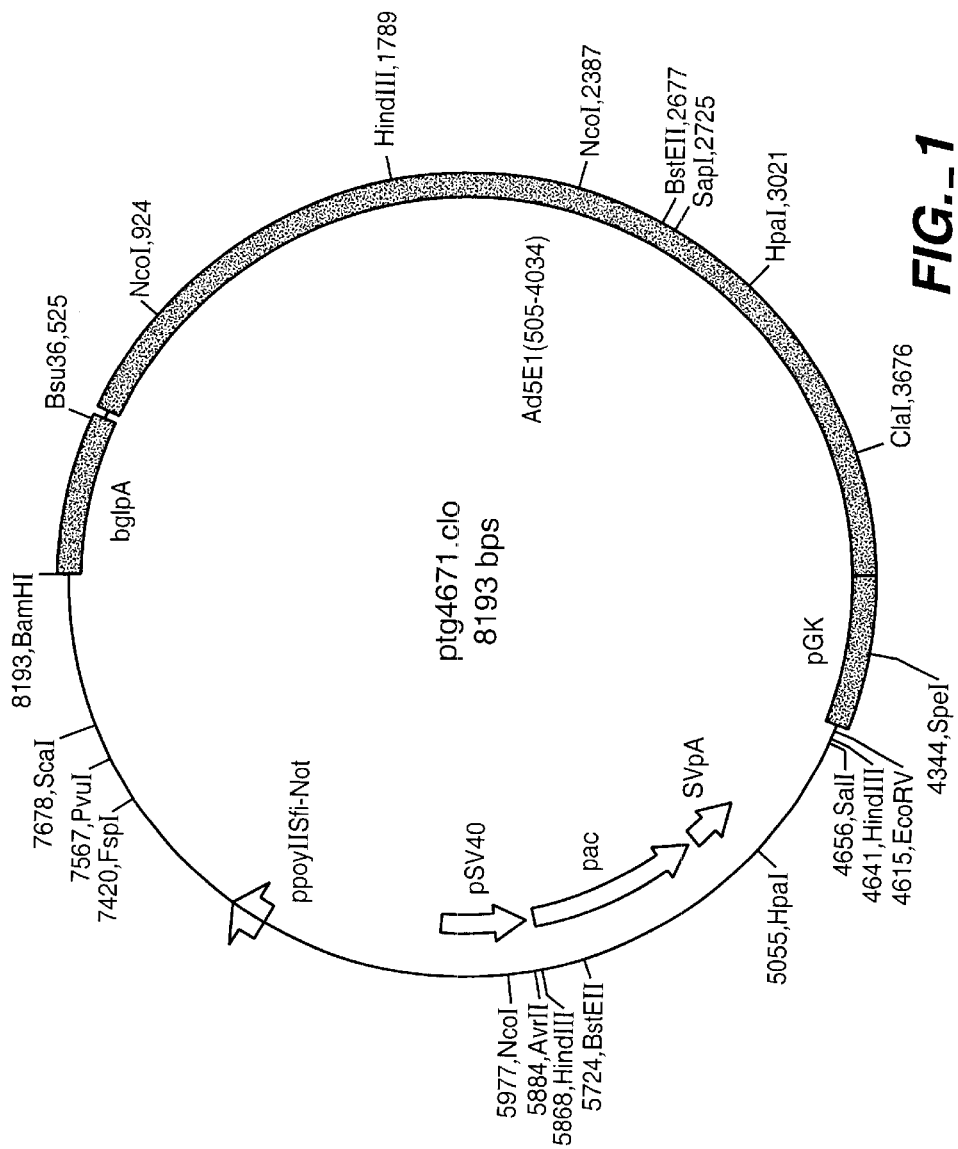
FIG. 1 shows a map of plasmid TG4671. Sequences from the human Adenovirus type 5 E1 region are indicated by the thick black line.

The practice of the present invention employs, unless otherwise indicated, conventional techniques of microbiology, immunology, virology, molecular biology, and recombinant DNA which are within the skill of the art. These techniques are fully explained in the literature. See, e.g., Maniatis et al., *Molecular Cloning: A Laboratory Manual* (1982); *DNA Cloning: A Practical Approach*, vols. I & II (D. Glover, ed.); *Oligonucleotide Synthesis* (N. Gait, ed. (1984)); *Nucleic Acid Hybridization* (B. Hames & S. Higgins, eds. (1985)); *Transcription and Translation* (B. Hames & S. Higgins, eds. (1984)); *Animal Cell Culture* (R. Freshney, ed. (1986)); Perbal, *A Practical Guide to Molecular Cloning* (1984); Ausubel, et al., *Current Protocols In Molecular Biology*, John Wiley & Sons (1987, and annual updates; and Sambrook et al., *Molecular Cloning: A Laboratory Manual* ($2^{nd}$ Edition); vols. I, II & III (1989).

B. Definitions

Operably linked or operatively linked refers to a juxtaposition of components (usually sequence elements) wherein the components are configured so as to perform their usual function. Thus, for example, a control sequence operably linked to a coding sequence is capable of affecting the expression of the coding sequence. The components need not be contiguous to one another so long as the control sequence is capable of exerting its normal regulatory function on the coding sequence.

Transformation or transfection refers to the process by which exogenous nucleic acid is introduced into a cell. Methods for introduction of nucleic acids into cells are well-known to those of skill in the art and include, for instance, microinjection, electroporation, $CaPO_4$ co-precipitation, DEAE-dextran-mediated transfer, lipid-mediated transfer, particle bombardment, etc.

Heterologous sequences refer to non-BAV sequences inserted into a recombinant BAV genome. In some cases, heterologous sequences will be sequences encoding all or part of a protein or polypeptide. In some cases, heterologous sequences will comprise a gene of interest or a fragment thereof.

The terms host cell and helper cell are used interchangeably to denote a cell or clone of cells capable of supporting the replication of an otherwise replication-defective adenovirus vector. Host cells generally provide an essential viral function for which the adenovirus vector is deficient. The term cell line can be used to refer to a clone of host cells.

C. Host Cells and Cell lines

The invention includes a cell or cell line which provides an essential viral function, such that a viral vector lacking that function can be propagated in the cell or cell line. In one embodiment, the viral vector is an adenovirus vector and the essential viral function provided by the cell line is an adenoviral function. Thus, in one embodiment, a cell or cell line is capable of producing at least some of the proteins required for replication of a defective adenoviral vector which the vector itself cannot produce. The protein provided by the cell or cell line can also be a structural protein, required for maturation and/or assembly of the viral particle. The protein can be involved in replication, transcription, regulation of these processes or any other essential viral function. The viral function provided by the cell line does not necessarily have to encode a protein, it could also encode an essential RNA.

The essential function, in one embodiment, is encoded by a fragment of an adenovirus genome, which can be modified by mutation, such as deletion and/or addition of nucleotides, point mutation, translocation, inversion, or rearrangement, as long as the mutation does not impair the capacity of the adenoviral genome fragment to complement a deficiency in a defective adenoviral vector. The adenoviral genome fragment can be present in the cell of the invention in a plasmid or viral vector or, preferably, can be integrated into the genome of the cell. Methods for introducing a fragment of an adenoviral genome into a vector, vectors suitable for such purposes, methods for introducing a vector or a nucleic acid fragment into a cell, and methods for directing integration of a nucleic acid fragment into a cellular genome are conventional techniques that are well-known to those of skill in the art. Thus, a stable helper cell line, expressing adenovirus functions encoded by adenovirus nucleic acid fragment(s) can be established. In the construction of such cell lines, co-transfection (of an adenoviral genome fragment or a vector containing an adenoviral genome fragment) with a selectable marker (such as a gene conferring antibiotic resistance) can be used to aid in detection of transfected cells. In some cases, the helper cell line can be established without the use of a separate selectable marker, based on the transforming capabilities of the products expressed by the adenoviral genome fragment. See, for example, FIG. 2.

In a preferred embodiment, the adenoviral function is E1 function and the adenoviral vector comprises a defective E1 region. The defect can be a point mutation, substitution, deletion, insertion, sequence rearrangement or any other type of genetic modification resulting in loss of function. Preferably, the defect is a deletion in the E1 region.

Thus, in one embodiment, the cells and cell lines of the invention are capable of providing E1A, E1B or both E1A and E1B functions of an adenovirus. In a preferred embodiment, the cells and cell lines of the invention comprise adenoviral sequences encoding the aforementioned functions. More preferably, the cells and cell lines of the invention express E1A and E1B functions encoded by a human adenovirus, such as, for example, human adenovirus type 5 (HAd-5). In these embodiments, human adenovirus E1 sequences can extend from the initiation (ATG) codon of the most upstream E1A-encoded polypeptide through the stop codon of the most downstream E1B-encoded polypeptide. However, the E1 sequences can also comprise additional adenoviral sequences at either of the 5' or 3' extremities, or both. In a preferred embodiment, the cells and cell lines of the invention comprise E1 sequences extending from nucleotides 505–4034 of the HAd-5 genome. In another embodiment, the cells and cell lines of the invention comprise E1 sequences extending from nucleotides 505–3510 of the HAd-5 genome. The complete sequence of the HAd-5 genome is known to those of skill in the art. Chroboczek et al. (1992) *Virology* 186:280–285.

Adenoviral sequences, present in a cell of the invention, can be placed in operative linkage with suitable control elements, both transcriptional and/or translational. Control elements can include those normally associated with the adenoviral sequences, or heterologous sequences. For example, adenoviral sequences present in a cell of the invention can retain the E1A promoter sequences and the E1B polyadenylation signal. In another embodiment, the adenoviral sequences are placed under the control of a suitable heterologous promoter which is functional in a helper cell line of the invention. The use of a heterologous polyadenylation site is also contemplated. Heterologous regulatory elements can be isolated from any eukaryotic or viral genome. Transcriptional regulatory elements, such as promoters, can be constitutive or regulatable. A regulatable control element can be either positively or negatively regulated, or both.

In one embodiment of the invention, recombinant cell lines are produced by constructing an expression cassette comprising an adenoviral E1 region and transforming host cells therewith to provide complementing cell lines or cultures expressing E1 function. These recombinant complementing cell lines are capable of allowing a defective recombinant adenovirus with deleted E1 sequences to replicate and express a desired foreign gene or fragment thereof which is optionally encoded within the recombinant adenovirus. The replication of defective recombinant adenoviruses with deleted E1 sequences and inserted heterologous sequences in a cell or cell line of the invention results in the production of infectious virions capable of expressing the heterologous sequence.

Recombinant complementing cell lines according to the invention are capable of allowing a defective recombinant BAV, having a deleted E1 gene region, wherein the deleted sequences are optionally replaced by heterologous nucleotide sequences, to replicate and express one or more foreign genes or fragments thereof encoded by the heterologous nucleotide sequences. BAV vectors with E1 deletions, wherein heterologous sequences are inserted in regions other than E1, can also be propagated in these complementing cell lines, and will express the heterologous sequences if they are inserted downstream of a BAV promoter or are inserted in operative linkage with a eukaryotic regulatory sequence. For example, cells and cell lines of the invention are useful in generating recombinant adenoviruses additionally comprising an E3 gene deletion, with the heterologous nucleotide sequence encoding a foreign gene or fragment thereof inserted in place of the deleted E3 region.

Preferred helper cell lines include VIDO-R2 cells, as described in Example 1, infra. Briefly, the VIDO R2 cell line is a fetal bovine retinal cell line that has been transfected with DNA from the human adenovirus type 5 (HAd-5) E1 region, and which supports the growth of E1-deleted BAV vectors and E1-deleted human adenoviruses. The present invention shows that the human adenovirus E1 polypeptides produced by VIDO-R2 cells are capable of complementing bovine adenoviruses deficient in E1 function. However, the risk of generating replication-competent, recombinant virus is reduced due to the differences in nucleotide sequence between the HAd and BAV E1 regions. Therefore, E1-deleted BAV vectors can be grown in VIDO-R2 cells without the risk of generating wild-type BAV by recombination.

More generally, defective recombinant BAV vectors, lacking one or more essential functions, can be propagated in appropriate complementing cell lines, wherein a particular complementing cell line provides a function or functions that is (are) lacking in a particular defective recombinant BAV vector. Complementing cell lines can provide viral functions through, for example, co-infection with a helper virus which expresses the function that the vector lacks, or by integrating or otherwise maintaining in stable form a fragment of a viral genome encoding a particular viral function.

The invention also includes a BAV vector that has been constructed using the host cells of the invention, and expression systems comprising said BAV vectors. In certain embodiments, a BAV vector constructed using the host cells of the invention will comprise one or more heterologous nucleotide sequences. That is, non-BAV sequences can replace part or all of the E3 region, part or all of the E1 region, part or all of the E2 region, part or all of the E4 region, part or all of the region between E4 and the right end of the genome, part or all of the late regions (L1–L7) and/or part or all of the regions occupied by the 33 kD, 52 kD, 100 kD, DBP, pol, pTP and penton genes, and genes IIIA, pV, pVI, pVII, pVIII and pX. Any of the aforementioned regions of the genome can be mutated or deleted, along with or instead of the E1 region. The expression system can be used wherein the heterologous nucleotide sequences are optionally under the control of any other heterologous promoter. BAV vectors can also comprise inverted terminal repeat (ITR) sequences and packaging sequences.

The BAV 33 kD, 52 kD, 100 kD, DBP, pTP, penton (III), pIIIA, pIVa2, pV, pVI, pVII, pVIII and pX genes are essential for viral replication. BAV vectors comprising deletions in any of these genes, or which lack functions encoded by any of these genes, can be used in the practice of the invention. However, such vectors must be grown in an appropriate complementing host cell (i.e., a helper cell line) providing the essential viral function(s) missing in the vector. In human adenoviruses, certain open reading frames in the E4 region (ORF 3 and ORF 6/7) are essential for viral replication. Deletions in analogous open reading frames in the E4 region of BAV-3 could necessitate the use of a helper cell line for growth of the viral vector. Accordingly, host cells providing any of the functions encoded by the genes described above are useful in the practice of the invention. Preferred host cell lines comprise sequences encoding the human adenovirus counterparts of these BAV genes.

The cell lines and host cells of the invention can be derived from any tissue of any mammalian species. A preferred species of cell is bovine cells. Preferred among bovine cells are those from kidney and fetal retina.

D. Adenoviral Vectors

In one embodiment of the invention, a recombinant expression cassette can be introduced within a BAV vector by cleaving a wild-type BAV genome with one or more appropriate restriction enzyme(s) to produce a BAV restriction fragment comprising E1 or E3 region sequences, respectively. The BAV restriction fragment can be inserted into a cloning vehicle, such as a plasmid, and thereafter at least one heterologous sequence (which may or may not encode a foreign protein), optionally in operative linkage with eukaryotic transcriptional and/or translational regulatory sequences, can be inserted into the E1 or E3 region. The resulting plasmid or linearized fragment is contacted with a BAV genome and, through homologous recombination or other conventional genetic engineering methods, the desired recombinant is obtained. The general methodology is described, for example, in Chartier et al. (1996) *J. Virol.* 70:4805–4810. Recombination between the expression cassette and a BAV genome can occur within an appropriate helper cell line such as, for example, a procaryotic cell or an E1-transformed cell line, such as that described by Graham et al. (199 1) In *Methods in Molecular Biology*, Vol. 7, Humana Press, pp. 109–128. Heterologous sequences can also be introduced into the BAV genome at sites other than the E1 and E3 regions. It is within the skill of the art to isolate a restriction fragment bearing a region of the BAV genome into which insertion of heterologous sequences is desired, to clone heterologous sequences into such an isolated fragment of the BAV genome, and to reintroduce an isolated BAV fragment containing heterologous sequences into a BAV genome to generate a BAV vector, either before or after transformation or transfection of an appropriate host cell.

Suitable host cells for construction of a BAV vector include any cell susceptible to transfection by BAV sequences (including a BAV genome) that will support recombination between a BAV genome and a plasmid containing BAV sequences (optionally comprising heterologous sequences), or between two or more plasmids, each containing BAV sequences (one or both of which optionally comprises heterologous sequences). Recombination is preferably performed in procaryotic cells, such as *E. coli*, while transfection of a viral genome (optionally contained in a plasmid) to generate virus particles is conducted in eukaryotic cells, preferably mammalian cells, more preferably bovine cells, still more preferably MDBK or PFBR cells, most preferably VIDO-R2 cells. The growth of bacterial cell cultures, as well as culture and maintenance of eukaryotic cells and mammalian cell lines are procedures which are well-known to those of skill in the art.

One or more heterologous sequences can be inserted into one or more regions of a BAV genome to generate a recombinant BAV vector, limited only by the insertion capacity of the BAV genome and ability of the recombinant BAV vector to express the inserted heterologous sequences. Regions of the BAV genome suitable for insertion of heterologous sequences include part or all of the E3 region, part or all of the E1 region, part or all of the E2 region, part or all of the E4 region, part or all of the region between E4 and the right end of the genome, part or all of the late regions (L1–L7) and/or part or all of the regions occupied by the 33 kD, 52 kD, 100 kD, DBP, pol, pTP and penton genes, and genes IIIA, pV, pVI, pVII, pVIII and pX. In general, adenovirus genomes of approximately 105% of normal genome length remain capable of being packaged into virus particles. The insertion capacity can be increased by deletion of non-essential regions and/or deletion of essential regions whose function is provided by a helper cell line or a helper virus. Accordingly, the insertion capacity of a vector can depend upon the nature and extent of the viral function(s) provided in trans: in the sense that the greater the number of essential viral functions provided by the helper cell line or helper virus, the larger the portion of the vector genome that can be deleted; hence, the higher the capacity of the vector.

In one embodiment of the invention, insertion can be achieved by constructing a plasmid containing the region of the BAV genome into which insertion is desired. The plasmid is then digested with one or more restriction enzymes having a recognition sequence in the BAV portion of the plasmid, and a heterologous sequence is inserted at the site of restriction digestion. The plasmid (or a linear fragment), containing a portion of the BAV genome with an inserted heterologous sequence, is co-transformed, along with a BAV genome or a linearized fragment containing a BAV genome, into a bacterial cell (such as, for example, E. coli), wherein the BAV genome can be a full-length genome or can contain one or more deletions. Homologous recombination between the plasmids (and/or fragments) generates a plasmid (or a fragment) comprising a recombinant BAV genome containing inserted heterologous sequences.

In another embodiment of the invention, a recombinant expression cassette can be obtained by cleaving a BAV genome with an appropriate restriction enzyme to produce a DNA fragment representing the left end or the right end of the genome comprising E1 or E3 sequences, respectively, and inserting the left- or right-end fragment into a cloning vehicle, such as a plasmid, and thereafter inserting at least one heterologous DNA sequence into the E1 or E3 sequence, the heterologous sequence optionally in operative linkage with an exogenous transcriptional regulatory sequence. The recombinant expression cassette is contacted with a BAV genome within an appropriate cell and, through homologous recombination or other conventional genetic engineering methods, a recombinant BAV genome is obtained. Appropriate cells include both prokaryotic cells, such as, for example, E. coli, and eukaryotic cells. Examples of suitable eukaryotic cells include, but are not limited to, MDBK cells, MDBK cells expressing adenovirus E1 function, primary fetal bovine retina cells, primary fetal bovine retina cells expressing adenovirus E1 function (such as VIDO-R2 cells) and cells expressing functions that are equivalent to those of the previously-recited cells.

Restriction fragments of the BAV genome other than those comprising the E1 and E3 regions are also useful in the practice of the invention and can be inserted into a cloning vehicle such that heterologous sequences may be inserted into sequences other that the E1 and E3 regions. These DNA constructs can then undergo recombination in vitro or in vivo, with a BAV genome, either before or after transformation or transfection of a suitable host cell as described above. For the purposes of the present invention, a BAV genome can be either a full-length genome or a genome containing a deletion in a region other than that deleted in the fragment with which it recombines, as long as the resulting recombinant BAV genome contains BAV sequences required for replication and packaging.

Methods for transfection, cell culture and recombination in procaryotic and eukaryotic cells such as those described above are well-known to those of skill in the art.

Deletion of BAV sequences, to provide a site for insertion of heterologous sequences or to provide additional capacity for insertion at a different site, can be accomplished by methods well-known to those of skill in the art. For example, for BAV sequences cloned in a plasmid, digestion with one or more restriction enzymes (with at least one recognition sequence in the BAV insert) followed by ligation will, in some cases, result in deletion of sequences between the restriction enzyme recognition sites. Alternatively, digestion at a single restriction enzyme recognition site within the BAV insert, followed by exonuclease treatment, followed by ligation will result in deletion of BAV sequences adjacent to the restriction site. A plasmid containing one or more portions of the BAV genome with one or more deletions, constructed as described above, can be co-transfected into a bacterial cell along with a BAV genome (full-length or deleted) or a plasmid containing either a full-length or a deleted BAV genome to generate, by homologous recombination, a plasmid containing a recombinant BAV genome with a deletion at one or more specific sites. BAV virions containing the deletion can then be obtained by transfection of mammalian cells (including, but not limited to, MDBK, PFBR and VIDO-R2 cells and their equivalents) with the plasmid containing the recombinant BAV genome.

In one embodiment of the invention, insertion sites are adjacent to and downstream (in the transcriptional sense) of BAV promoters. Locations of BAV promoters, and restriction enzyme recognition sequences downstream of BAV promoters, for use as insertion sites, can be easily determined by one of skill in the art from the BAV nucleotide sequence provided in co-owned International Patent Applications PCT/CA94/00678 and PCT/CA98/00624. Alternatively, various in vitro techniques can be used for insertion of a restriction enzyme recognition sequence at a particular site, or for insertion of heterologous sequences at a site that does not contain a restriction enzyme recognition sequence. Such methods include, but are not limited to, oligonucleotide-mediated heteroduplex formation for insertion of one or more restriction enzyme recognition sequences (see, for example, Zoller et al. (1982) *Nucleic Acids Res.* 10:6487–6500; Brennan etal. (1990) *Roux's Arch. Dev. Biol.* 199:89–96; and Kunkel et al. (1987) *Meth. Enzymology* 154:367–382) and PCR-mediated methods for insertion of longer sequences. See, for example, Zheng et al. (1994) *Virus Research* 31:163–186.

It is also possible to obtain expression of a heterologous sequence inserted at a site that is not downstream from a BAV promoter, if the heterologous sequence additionally comprises transcriptional regulatory sequences that are active in eukaryotic cells. Such transcriptional regulatory sequences can include cellular promoters such as, for example, the bovine hsp70 promoter and viral promoters such as, for example, herpesvirus, adenovirus and papovavirus promoters and DNA copies of retroviral long terminal repeat (LTR) sequences.

In another embodiment, homologous recombination in a procaryotic cell can be used to generate a cloned BAV genome comprising an E1 deletion; and the cloned, E1-deleted BAV genome can be propagated as a plasmid. Infectious virus can be obtained by transfection of VIDO-R2 cells, or their equivalents, with the cloned, E1-deleted BAV genome rescued from plasmid-containing cells.

The host cells of the invention, which provide essential viral functions, can be used for expression of proteins or peptides encoded by heterologous sequences included in recombinant BAV vectors. Methods for expression and purification of recombinant proteins and peptides are well-known to those of skill in the art; e.g., Ausubel et al., supra.

Additional methods for preparation of recombinant adenoviral genomes, including BAV genomes, by recombination in a procaryotic cell, and transformation of mammalian cells (including bovine cells) with the recombinant genomes so generated, to generate recombinant adenovirus vectors, are described in co-owned International applications PCT/CA94/00678 and PCT/CA98/00624, the disclosures of which are hereby incorporated by reference in their entireties.

E. Therapeutic Genes and Polypeptides

BAV vectors that are propagated using the cells and cell lines of the invention can be used for the expression of therapeutic polypeptides and nucleic acids in applications such as in vitro polypeptide production, vaccine production, nucleic acid immunization and gene therapy, for example.

In one embodiment, BAV vectors propagated in the host cells of the invention will contain heterologous sequences encoding protective determinants of various mammalian pathogens, for use in subunit vaccines and nucleic acid immunization. Representative mammalian pathogen antigens include, but are not limited to, bacterial pathogens, such as Pasteurella sp. and Hemophilus sp.; and viral pathogens, such as herpesviruses, influenzaviruses, parainfluenzaviruses, rotaviruses, coronaviruses, viral diarrhea viruses, picornaviruses, adenoviruses, retroviruses, lentiviruses, etc. BAV vectors can also include genes encoding cytokines, such as interferons, interleukins and colony-stimulating factors (either instead of or in addition to sequences encoding protective determinants) and therapeutic polypeptides such as the cystic fibrosis transmembrane conductance regulator (CFTR) and coagulation factor IX, for example.

Various foreign genes or nucleotide sequences or coding sequences (prokaryotic or eukaryotic) can be inserted into a BAV vector that is propagated in accordance with the present invention, particularly to provide protection against a wide range of diseases. Protection can be provided by way of subunit vaccines, nucleic acid immunization and/or gene therapy, using recombinant vectors propagated according to the methods of the invention.

A heterologous (ie., foreign) nucleotide sequence can consist of one or more gene(s) of interest, and preferably of therapeutic interest. In the context of the present invention, a gene of interest can encode a structural RNA, a ribosomal RNA, an antisense RNA, a ribozyme or it can encode an mRNA which will then be translated into a protein of interest. A gene of interest can be of genomic type, of complementary DNA (cDNA) type or of mixed type (i.e., a minigene, in which at least one intron is deleted). It can code for a mature protein; a precursor of a mature protein, in particular a precursor intended to be secreted and accordingly comprising a signal peptide; a chimeric protein originating from the fusion of sequences of diverse origins; or a mutant of a natural protein displaying improved or modified biological properties. Such a mutant can be obtained by deletion, substitution and/or addition of one or more nucleotide(s) of the gene coding for the natural protein, or any other type of change in the sequence encoding the natural protein, such as, for example, transposition or inversion.

A gene of interest can be placed under the control of regulatory sequences suitable for its expression in a host cell. Suitable regulatory sequences are understood to mean the set of elements needed for transcription of a gene into RNA (structural, ribosomal, ribozyme, antisense RNA or mRNA), for processing of RNA, and for the translation of an mRNA into protein. Among the elements needed for transcription, the promoter assumes special importance. It can be a constitutive promoter or a regulatable promoter, and can be isolated from any gene of eukaryotic, prokaryotic or viral origin, and even adenoviral origin. Alternatively, it can be the natural promoter of the gene of interest. Generally speaking, a promoter used in the present invention can be chosen to contain cell-specific regulatory sequences, or modified to contain such sequences. For example, a gene of interest for use in the present invention is placed under the control of an immunoglobulin gene promoter when it is desired to target its expression to lymphocytic host cells. There may also be mentioned the HSV-1 TK (herpesvirus type 1 thymidine kinase) gene promoter, the adenoviral MLP (major late promoter), in particular of human adenovirus type 2, the RSV (Rous Sarcoma Virus) LTR (long terminal repeat), the CMV (Cytomegalovirus) early promoter, and the PGK (phosphoglycerate kinase) gene promoter, for example, permitting expression in a large number of cell types.

In addition to promoters, enhancer sequences are also important in regulating the degree of expression of a gene or coding sequence to which they are operatively linked. A heterologous gene or coding sequence can be regulated by an endogenous adenoviral enhancer present in the vector, or can be regulated by a non-vector enhancer. A non-vector enhancer can be an enhancer normally associated with the heterologous gene in its natural state, or one that is not normally associated with the gene or coding sequence, but is placed in operative linkage with the gene or coding sequence by in vitro techniques.

Alternatively, targeting of a recombinant BAV vector to a particular cell type can be achieved by constructing recombinant hexon and/or fiber genes. The protein products of these genes are involved in host cell recognition; therefore, the genes can be modified to contain peptide sequences that will allow the virus to recognize alternative host cells.

Among genes of interest which are useful in the context of the present invention, there may be mentioned:

genes coding for cytokines such as interferons and interleukins;

genes encoding lymphokines;

genes coding for membrane receptors such as the receptors recognized by pathogenic organisms (viruses, bacteria or parasites), preferably by the HIV virus (human immunodeficiency virus);

genes coding for coagulation factors such as factor VIII and factor IX;

genes coding for dystrophins;

genes coding for insulin;

genes coding for proteins participating directly or indirectly in cellular ion channels, such as the CFTR (cystic fibrosis transmembrane conductance regulator) protein;

genes coding for antisense RNAs, or proteins capable of inhibiting the activity of a protein produced by a pathogenic gene which is present in the genome of a pathogenic organism, or proteins (or genes encoding them) capable of inhibiting the activity of a cellular gene whose expression is deregulated, for example an oncogene;

genes coding for a protein inhibiting an enzyme activity, such as $\alpha_1$-antitrypsin or a viral protease inhibitor, for example;

genes coding for variants of pathogenic proteins which have been mutated so as to impair their biological function, such as, for example, trans-dominant variants of the tat protein of the HIV virus which are capable of competing with the natural protein for binding to the target sequence, thereby preventing the activation of HIV;

genes coding for antigenic epitopes in order to increase the host cell's immunity;

genes coding for major histocompatibility complex classes I and II proteins, as well as the genes coding for the proteins which are inducers of these genes;

genes coding for antibodies;

genes coding for immunotoxins;

genes encoding toxins;

genes encoding growth factors or growth hormones;

genes encoding cell receptors and their ligands;

genes encoding tumor suppressors;

genes coding for cellular enzymes or those produced by pathogenic organisms; and suicide genes. The HSV-1 TK suicide gene may be mentioned as an example. This viral TK enzyme displays markedly greater affinity compared to the cellular TK enzyme for certain nucleoside analogues (such as acyclovir or gancyclovir). It converts them to monophosphorylated molecules, which can themselves be converted by cellular enzymes to nucleotide precursors, which are toxic. These nucleotide analogues can be incorporated into replicating DNA molecules, hence incorporation occurs chiefly in the DNA of dividing cells. This incorporation can result in specific destruction of dividing cells such as cancer cells.

Although any gene or coding sequence of therapeutic relevance can be used in the practice of the invention, certain genes, or fragments thereof, are particularly suitable. For example, genes encoding immunogenic polypeptides, toxins, immunotoxins and cytokines are useful in the practice of the invention. Cytokine genes of use in the invention include, but are not limited to, those encoding $\alpha$, $\beta$ or $\gamma$ interferon (IFN), interleukins (IL) such as IL-2, IL-6, IL-10 or IL-12, tumor necrosis factor (TNF), colony stimulating factors such as GM-CSF, C-CSF, M-CSF, and other cytokines as are known to those of skill in the art. Additional genes include those encoding cell or nuclear receptors and their ligands (e.g.,fas ligand), coagulation factors (for example, FVIII, FIX), growth hormones, growth factors such as fibroblast growth factors (FGF), vascular endothelial growth factors (VEGF), nerve growth factors (NGF), epidermal growth factors (EGF), platelet-derived growth factors (PDGF) and other growth factors as are known to those of skill in the art. Genes suitable for use in the practice of the invention can encode enzymes (such as, for example, urease, renin, thrombin, metalloproteases, nitric oxide synthase, superoxide dismutase, catalase and others known to those of skill in the art), enzyme inhibitors (such as, for example, $\alpha$1-antitrypsin, antithrombin III, cellular or viral protease inhibitors, plasminogen activator inhibitor-1, tissue inhibitor of metalloproteases, etc.), the cystic fibrosis transmembrane conductance regulator (CFTR) protein, insulin, dystrophin, or a Major Histocompatibility Complex (MHC) antigen of class I or II. Also useful are genes encoding polypeptides that can modulate/regulate expression of corresponding genes, polypeptides capable of inhibiting a bacterial, parasitic or viral infection or its development (for example, antigenic polypeptides, antigenic epitopes, and transdominant protein variants inhibiting the action of a native protein by competition), apoptosis inducers or inhibitors (for example, Bax, Bcl2, BclX and others known to those of skill in the art), cytostatic agents (e.g., p21, p16, Rb, etc.), apolipoproteins (e.g., ApoAI, ApoAIV, ApoE, etc.), angiogenesis inhibitors (e.g., angiostatin, endostatin, etc.), oxygen radical scavengers, polypeptides having an anti-tumor effect, antibodies, toxins, immunotoxins, markers (e.g., $\beta$-galactosidase, luciferase, etc.) or any other genes of interest that are recognized in the art as being useful for treatment or prevention of a clinical condition.

For example, with respect to treating hereditary dysfunctions, one may use a functional copy of a defective gene, for example a gene encoding factor VIII or IX in the context of haemophilia A or B, dystrophin (or minidystrophin) in the context of myopathies, insulin in the context of diabetes, or CFTR (Cystic Fibrosis Transmembrane Conductance Regulator) in the context of cystic fibrosis. Suitable genes of interest to delay or inhibit tumor or cancer progression, include but are not limited to those encoding an antisense RNA, a ribozyme, a cytotoxic product such as thymidine kinase of herpes simplex virus type 1 (HSV-1 TK), ricin, a bacterial toxin, the products of the yeast genes FCY1 and/or FUR1 having CDase (cytosine deaminase) and UPRTase (uracil phosphoribosyl transferase) activities respectively, an antibody, a polypeptide inhibiting cellular division or signal transduction, a tumor suppressor gene (such as, for example, p53, Rb, p73), a polypeptide which activates the host immune system, a tumor-associated antigen (e.g., MUC-1, BRCA-1, an HPV early or late antigen such as E6, E7, L1, L2, etc), optionally in combination with a cytokine gene. Finally, in the context of anti-HIV therapy, one may use a gene encoding an immunoprotective polypeptide, an antigenic epitope, an antibody (2F5; Buchacher et al., 1992, *Vaccines* 92:191–195), the extracellular domain of CD4 (sCD4; Traunecker et al., 1988, *Nature* 331:84–86), an immunoadhesin (i.e., a CD4-IgG hybrid, CD4-2F5 fusion; Capon et al., 1989, *Nature* 337:525–531; Byrn et al., 1990, *Nature* 344:667–670), an immunotoxin (i.e., resulting from fusion between angiogenin and 2F5 or CD4-2F5; Kurachi et al., 1985, *Biochemistry* 24:5494–5499), a trans-dominant variant (EP 0614980, WO95/16780), a cytotoxic product (see above) or IFN$\alpha$ or $\beta$.

In addition, a gene of interest may also encode all or part of a selective marker, allowing the selection of transfected and transduced cells. Such genes include but are not limited to the neo gene (encoding neomycin phosphotransferase) conferring resistance to G418, dhfr (Dihydrofolate Reductase), CAT (Chloramphenicol Acetyl Transferase), pac (Puromycin Acetyl-Transferase) and gpt (Xanthine Guanine Phosphoribosyl Transferase). Genes encoding selective markers are known in the art.

The above-mentioned genes and coding regions, as well as others known to those of skill in the art, are suitable for use in any aspect of the invention, including protein production, vaccination, nucleic acid immunization and/or gene therapy, among others.

This above list is not restrictive, and any other gene of interest can be used in the context of the present invention. In some cases the gene for a particular antigen can contain a large number of introns or can be from an RNA virus, in these cases a complementary DNA copy (cDNA) of the gene transcript or of the viral genome can be used. It is also possible that only fragments of nucleotide sequences of genes can be used (where these are sufficient to generate a protective immune response or a specific biological effect) rather than the complete sequence as found in the wild-type organism. Where available, synthetic genes or fragments thereof can also be used. However, the present invention can be used with a wide variety of genes, fragments and the like, and is not limited to those set out above.

Recombinant BAV vectors propagated in the host cells of the invention can be used to express antigens for provision of, for example, subunit vaccines. Antigens used in the present invention can be either native or recombinant antigenic polypeptides or fragments. They can be partial sequences, full-length sequences, or fusions (e.g., having appropriate leader sequences for the recombinant host, or with an additional antigen sequence for another pathogen). The preferred antigenic polypeptide to be expressed by the virus systems of the present invention contains full-length (or near full-length) sequences encoding antigens. Alternatively, shorter sequences that are antigenic (i.e., encode one or more epitopes) can be used. The shorter sequence can encode a "neutralizing epitope," which is defined as an epitope capable of eliciting antibodies that neutralize virus infectivity in an in vitro assay. Preferably the peptide should encode a "protective epitope" that is capable of raising in the host a "protective immune response;" i.e., a humoral (i.e. antibody-mediated), cell-mediated, and/or mucosal immune response that protects an immunized host from infection.

F. Therapeutic Applications

With the recombinant viruses produced using the host cells of the present invention, it is possible to provide protection against a wide variety of diseases affecting mammals. Any of the recombinant antigenic determinants or recombinant live virus vectors propagated according to the methods of the invention can be formulated and used in substantially the same manner as described for antigenic determinant vaccines or live vaccine vectors.

Antigens expressed by vectors propagated according to the methods of the present invention, particularly when comprised of short oligopeptides, can be conjugated to a vaccine carrier. Vaccine carriers are well known in the art: for example, bovine serum albumin (BSA), human serum albumin (HSA) and keyhole limpet hemocyanin (KLH). A preferred carrier protein, rotavirus VP6, is disclosed in EPO Pub. No. 0259149, the disclosure of which is incorporated by reference herein.

Genes for desired antigens or coding sequences thereof which can be inserted include those of organisms which cause disease in mammals, particularly bacterial and viral pathogens. Genes encoding antigens of human pathogens are also useful in the practice of the invention. Representative mammalian pathogen antigens include, but are not limited to, bacterial pathogens, such as Pasteurella sp. and Hemophilus sp.; and viral pathogens, such as herpesviruses, influenzaviruses, parainfluenzaviruses, rotaviruses, coronaviruses, viral diarrhea viruses, picomaviruses, adenoviruses, retroviruses, lentiviruses, etc. BAV vectors can also include genes encoding cytokines, such as interferons, interleukins and colony-stimulating factors (either instead of or in addition to sequences encoding protective determinants) and therapeutic polypeptides such as the cystic fibrosis transmembrane conductance regulator (CFTR) and coagulation factor IX, for example.

The present invention also includes pharmaceutical compositions comprising a therapeutically effective amount of a recombinant vector, recombinant virus or recombinant protein, prepared according to the methods of the invention, in combination with a pharmaceutically acceptable vehicle and/or an adjuvant. Such a pharmaceutical composition can be prepared and dosages determined according to techniques that are well-known in the art. The pharmaceutical compositions of the invention can be administered by any known administration route including, but not limited to, systemically (for example, intravenously, intratracheally, intraperitoneally, intranasally, parenterally, enterically, intramuscularly, subcutaneously, intratumorally or intracranially) or by aerosolization or intrapulmonary instillation. Administration can take place in a single dose or in doses repeated one or more times after certain time intervals. The appropriate administration route and dosage will vary in accordance with the situation (for example, the individual being treated, the weight of the individual, the disorder to be treated or the gene or polypeptide of interest), but can be determined by one of skill in the art.

The vaccines of the invention carrying foreign genes or fragments can be orally administered in a suitable oral carrier, such as in an enteric-coated dosage form. Oral formulations include such normally-employed excipients as, for example, pharmaceutical grades of mannitol, lactose, starch, magnesium stearate, sodium saccharin cellulose, magnesium carbonate, and the like. Oral vaccine compositions may be taken in the form of solutions, suspensions, tablets, pills, capsules, sustained release formulations, or powders, containing from about 10% to about 95% of the active ingredient, preferably about 25% to about 70%. An oral vaccine may be preferable to raise mucosal immunity (which plays an important role in protection against pathogens infecting the gastrointestinal tract) in combination with systemic immunity.

In addition, the vaccine can be formulated into a suppository. For suppositories, the vaccine composition will include traditional binders and carriers, such as polyalkaline glycols or triglycerides. Such suppositories may be formed from mixtures containing the active ingredient in the range of about 0.5% to about 10% (w/w), preferably about 1% to about 2%.

Protocols for administering to mammals the vaccine composition(s) of the present invention are within the skill of the art in view of the present disclosure. Those skilled in the art will select a concentration of the vaccine composition in a dose effective to elicit antibody, cell-mediated and/or mucosal immune responses to the antigenic fragment. Within wide limits, the dosage is not believed to be critical. Typically, the vaccine composition is administered in a manner which Hwill deliver between about 1 to about 1,000 micrograms of the subunit antigen in a convenient volume of vehicle, e.g., about 1–10 ml. Preferably, the dosage in a single immunization will deliver from about 1 to about 500 micrograms of subunit antigen, more preferably about 5–10 to about 100–200 micrograms (e.g., 5–200 micrograms).

The timing of administration may also be important. For example, a primary inoculation preferably may be followed by subsequent booster inoculations, for example, several weeks to several months after the initial immunization, if needed. To insure sustained high levels of protection against disease, it may be helpful to readminister booster immunizations at regular intervals, for example once every several years. Alternatively, an initial dose may be administered orally followed by later inoculations, or vice versa. Preferred vaccination protocols can be established through routine vaccination protocol experiments.

A problem that has beset the use of adenovirus vectors for immunization and gene therapy in humans is the rapid development of an immunological response (or indeed in some cases existing immunity) to human adenoviruses (HAds). Recombinant BAV vectors are likely to be less immunogenic in humans and, for this and other reasons, will be useful either as a substitute for HAd vectors or in combination with HAd vectors. For example, an initial immunization with a HAd vector can be followed by booster immunizations using BAV vectors; alternatively, initial immunization with a recombinant BAV vector can be followed by booster immunizations with HAd and/or BAV vectors.

The dosage for all routes of administration of in vivo recombinant virus vaccine depends on various factors including, the size of patient, nature of infection against which protection is needed, carrier and the like and can readily be determined by those of skill in the art. By way of non-limiting example, a dosage of between approximately $10^3$ pfu and $10^{13}$ pfu, preferably $10^3$ to $10^{10}$ pfu, more preferably, $10^3$ to $10^8$ pfu can be used. As with in vitro subunit vaccines, additional dosages can be given as determined by the clinical factors involved.

The invention also encompasses a method of treatment, according to which a therapeutically effective amount of a BAV vector, recombinant BAV, or host cell of the invention is administered to a mammalian subject requiring treatment.

G. Gene Therapy

Recombinant adenovirus vectors and their genomes, produced using the host cells of the invention, can be used in methods for providing gene therapy to a mammal, to control a gene deficiency. In one embodiment, these methods comprise administering to said mammal a live recombinant BAV containing a heterologous nucleotide sequence encoding a non-defective form of a deficient gene, under conditions wherein the recombinant virus vector genome is incorporated into the mammalian genome or is maintained independently and extrachromosomally, to provide expression of the non-defective gene in a particular target organ or tissue. These and related techniques can also be used to replace a defective gene or portion thereof. Non-limiting examples of foreign genes, heterologous nucleotide sequences, or portions thereof that can be incorporated for use in gene therapy have been discussed above in section E, entitled "Therapeutic genes and polypeptides."

In particular, use of adenovirus vectors propagated in the host cells of the invention in regard to gene therapy in humans is intended for the prevention or treatment of diseases including, but not limited to, genetic diseases (for example, hemophilia, thalassemias, myopathies, muscular dystrophy, diabetes, emphysema, Gaucher's disease, cystic fibrosis, Duchenne muscular dystrophy, Duchenne's or Becker's myopathy, etc.), cancers, viral diseases (for example, AIDS, herpesvirus infection, Cytomegalovirus infection and papillomavirus infection), immune deficiency diseases, cardiovascular diseases, and the like. For the purposes of the present invention, the vectors, cells and viral particles prepared by the methods of the invention can be introduced into a subject either ex vivo, (i.e., in a cell or cells removed from the patient) or directly in vivo into the body to be treated, into any type of cell. Preferably, the host cell is a human cell and, more preferably, is a lung cell, an airway epithelial cell, a fibroblast, a muscle cell (including smooth muscle, striated muscle and cardiac muscle), a liver cell, a lymphocytic cell, a cell of the hematopoietic lineage, an endothelial cell or a malignantly transformed descendant of these or any other cell.

Described below are examples of the present invention. These examples are provided for illustrative purposes only and are not intended to limit the scope of the present invention in any way. In light of the present disclosure, numerous embodiments within the scope of the claims will be apparent to those of ordinary skill in the art. The contents of the references cited in the specification are incorporated by reference herein.

EXAMPLES

General Methods

BAV-3 was cultured in Madin-Darby bovine kidney (MDBK) cells or VIDO R2 cells grown in Eagle's minimal essential medium supplemented with 5% fetal bovine serum. Viral DNA was extracted from virus-infected cell monolayers by the method of Hirt (1967) *J. Mol. Biol.* 26:365–369. Recombinant plasmids were constructed by standard procedures using restriction endonucleases and other DNA modifying enzymes according to the manufacturers' instructions.

Example 1

Construction and Properties of the VIDO-R2 Cell Line

Primary cultures of fetal bovine retina cells (FBRC) were transfected with 10 μg of plasmid pTG4671 (Transgene) by calcium phosphate co-precipitation. This plasmid contains the entire E1A and E1B sequences (nucleotides 505–4034) of human adenovirus-5 (GenBank Accession No. M73260), with E1A transcription under the control of the constitutive mouse phosphoglycerate kinase promoter and E1B transcription under the control of its natural promoter and a β-globin polyadenylation signal. Chroboczek et al. (1992) *Virology* 186:280–285; Adra et al. (1987) *Gene* 60:65–74. A gene encoding the selectable marker puromycin acetyl transferase (pac), under the control of the constitutive SV40 early promoter and a SV40 polyadenylation signal, is also present in plasmid TG4671. See FIG. 1.

Transformed cells were cultured without selection for puromycin resistance. Four weeks after transfection, foci of transformed cells were observed. The transformed cells were smaller and rounder than untransformed cells. See FIG. 2. Transformed cells expressed vimentin, but not cytokeration, indicating that they are of mesenchymal origin. Cell foci were subjected to single cell cloning. One of the clones obtained was named VIDO R2.

Expression of E1 mRNA was examined by reverse transcription polymerase chain reaction (RT-PCR) analysis, using pairs of primers specific for the E1A- and E1B regions of HAV-5. RT-PCR using R2 cell RNA generated products that matched the size of PCR products generated from an E1 DNA template using the same primers. When reverse transcriptase was omitted from the RT-PCR reaction using R2 cell RNA, no product was observed, indicating that the amplification products were derived from E1 mRNAs and not residual DNA.

Expression of E1A and E1B proteins was analyzed by immunological analysis of protein blots (Western blotting), using mouse monoclonal antibody M73 to detect E1A proteins, and antibody 3D11 (Calbiochem, La Jolla, Calif.) to detect the 19 kDa HAV E1B protein. Both E1A (FIG. 3) and E1B (FIG. 4) polypeptides were produced by the VIDO-R2 cell line, and were not detected in the parental FBRC line.

Doubling time in cell culture was also determined for the R2 cell line. Visual inspection of cultures showed that VIDO-R2 cells formed monolayers within 2–3 days after plating a 1:3 dilution of confluent cells, while the parent PFBR cells required 10–15 days to form monolayers under the same conditions. PCR experiments, using VIDO-R2 cell genomic DNA as template, indicated that the E1 sequences present in VIDO-R2 were integrated into the cellular genome.

Example 2

Complementing Properties of VIDO R2 Cells

To investigate the complementing properties of the VIDO R2, the cells were infected with an E1A deletion mutant of HAV-5 (Ad5d1E1AlacZ). Zheng et al. (1994) *Virus Res.* 31:163–186. This cell line supported the growth of the deletion mutant to $10^7$ pfu/ml. To determine whether the VIDO R2 cell line could support plaque formation, cells cultured in 35-mm-diameter dishes were infected with BAV-3 or HAV-5 and incubated in a $CO_2$ incubator. Clear plaque formation was evident on day 5 and 7 postinfection with HAV-5 and BAV-3, respectively. A substantially more rapid onset of viral cytopathic effect was observed in E1-expressing cell lines as opposed to MDBK and FBRC lines. In addition, the R2 cell line supported formation of clear plaques by recombinant BAV-3.

Example 3

Transfection Ability of VIDO R2 Cells

To test the ability of the cells to take up large DNA, MDBK and VIDO R2 cells, in 35 mm-diameter dishes, were transfected with 1–3 ug of PacI-restricted plasmid pFBAV304 using Lipofectin (GIBCO/BRL). This plasmid contains the entire BAV-3 genome with the E3 region replaced by a green fluorescent protein (GFP)gene under the control of a cytomegalovirus immediate early promoter. See Example 7. When observed by fluorescence microscopy 24 hours following transfection, more than 3% of VIDO R2 cells showed fluorescence, as opposed to less than 0.1% of the cells in MDBK cultures. Further incubation of the transfected VIDO R2 cells for 10–14 days resulted in production of a recombinant virus (BAV 304) expressing GFP. These observations suggest that VIDO R2 cells are well-suited for generation of recombinant BAV-3, perhaps in part owing to higher transfection efficiency and/or the presence of HAV-5 E1A and E1B sequences.

Example 4

Construction of BAV3.500, a Replication-defective, Recombinant BAV with Deletions in E1 and E3

A BAV3 with a genome having deletions in the E1A and E3 regions was constructed as follows.

The plasmid pTG5435 (FIG. 5), comprising a full-length BAV-3 genome in a ppolyIIsn14 plasmid backbone (Lathe et al. (1987) *Gene* 57:193–201) was digested with HindII, and a 4.9 kb fragment harboring the terminal BAV-3 sequences was isolated and religated, creating plasmid pLt-Rt.Hind (pBAV-101). The plasmid pLt-Rt.Hind was digested with AccI and SpeI, generating 2 fragments, which were treated with T4 DNA polymerase to generate blunt ends. The larger fragment (4.4 kbp) was isolated and ligated to a XbaI linker to create plasmid pLR.Hind-XbaI (pBAV-102), containing a deletion in E1 with the deleted sequences replaced by an XbaI site. This plasmid was digested with HindIII, dephosphorylated, and the linear dephosphorylated fragment was gel-purified. The gel-purified fragment was recombined with genomic DNA of recombinant BAV.E3d (a BAV genome containing a 1.245 kb deletion inthe E3 region) by co-transformation of *E. coli*, to create plasmid pBAV3.500 (pFBAV500). See FIG. 6.

PacI-digested pFBAV500 DNA was transfected into VIDO-R2 cells (5–10 lig per 60 mm diameter dish of cell monolayer) using Lipofectin (GIBCO/BRL). After incubation at 37° C., cells showing cytopathic effects were collected and subjected to two cycles of freeze-thawing, and recombinant virus (BAV3.500) was plaque-purified on VIDO R2 cells.

Example 5

Construction of BAV3.501, a Replication-defective Recombinant BAV with an Insertion of the Bovine Herpesvirus Type 1 Glycoprotein D Gene in the E1A Region A BAV3 genome containing deletions in the E1A and E3 regions, with an insertion of BHV-1 gD in place of the deleted E1A sequences was constructed as follows. See FIG. 7.

Plasmid pBAV-102 (See Example 4) was digested with Xba I, treated with T4 DNA polymerase, dephosphorylated and gel-purified. A blunt-ended 1.8 kb fragment, containing the bovine herpesvirus type I (BHV-1) glycoprotein D (gD) gene, including a 137-nucleotide chimeric intron and flanked upstream by the SV40 early promoter and downstream by the SV40 late polyadenylation site, was ligated to the gel-purified XbaI fragment to create a plasmid. pLR.H-b.gD (pBAV-102 gD), containing a deletion in E1A with the deleted sequences replaced by the BHV-1 gD gene. This plasmid was recombined with genomic DNA of recombinant BAV.E3d (a BAV genome containing a 1.245 kb deletion in the E3 region) by co-transfection of *E. coli* BJ5183, to create plasmid pBAV3.501 (pFBAV501).

PacI-digested pFBAV501 DNA was transfected into VIDO-R2 cells (5–10 µg per 60 mm diameter dish of cell monolayer) using Lipofectin (GIBCO/BRL). After incubation at 37° C., cells showing cytopathic effects were collected and subjected to two cycles of freeze-thawing, and recombinant virus (BAV3.501) was plaque-purified on VIDO R2 cells.

The presence of the gD insert was confirmed by Cla I digestion, which indicated the loss of a 2.5 kb fragment characteristic of BAV3.500 and its replacement by a fragment of 4.4 kb. Southern blot analysis with a gD probe confirmed that gD sequences were present in the 4.4 kb fragment.

Example 6

Figure 8:
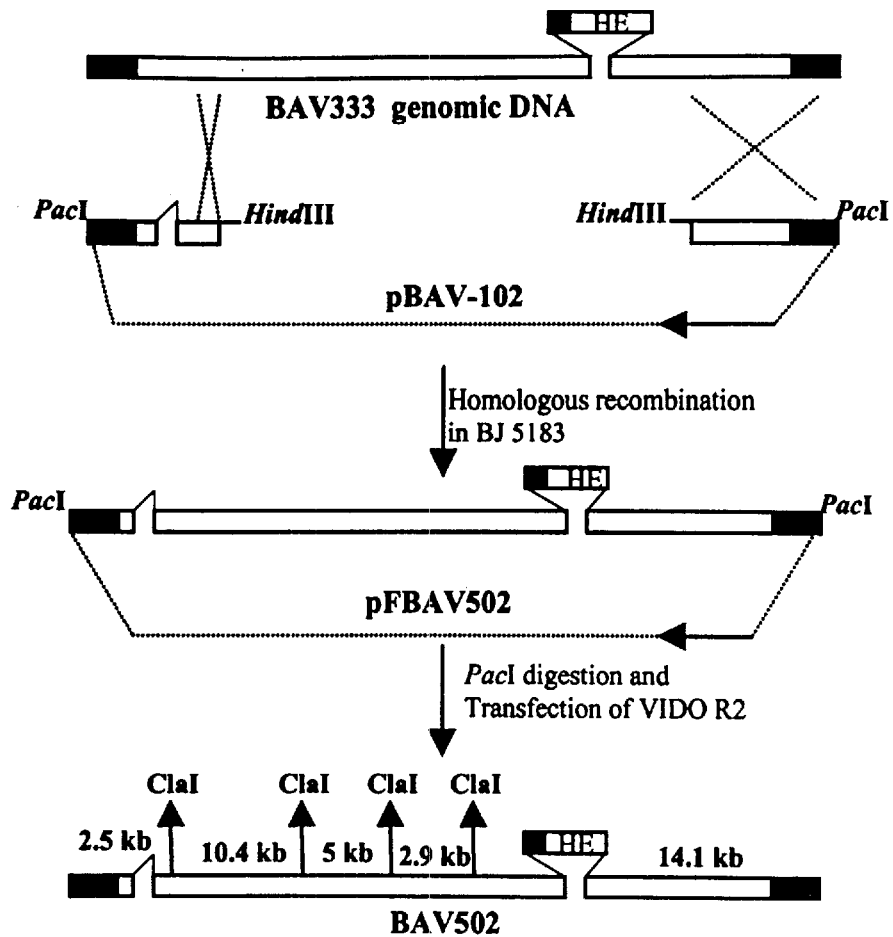
FIG. 8 is a schematic diagram showing the construction of BAV3.502. See Example 6.

Construction of BAV3.502, a Replication-defective Recombinant BAV with an Insertion of the Bovine Coronavirus HE Gene in the E3 Region A recombinant BAV genome, containing an insertion of the bovine coronavirus (BCV) hemagglutinin-esterase (HE) gene in the E3 region, in the same transcriptional orientation as E3, was constructed as follows. See FIG. 8.

The BCV HE gene insert contained a 137-nucleotide chimeric intron and was flanked by the SV40 early promoter and a SV40 polyadenylation site. This recombinant genome was introduced into *E. coli* BJ5183, along with HindIII-digested pBAV-102. In vivo recombination between these two DNA molecules generated pFBAV502.

PacI-digested pFBAV502 DNA was transfected into VIDO-R2 cells (5–10 µg per 60 mm diameter dish of cell monolayer) using Lipofectin (GIBCO/BRL). After incubation at 37° C., cells showing cytopathic effects were collected and subjected to two cycles of freeze-thawing, and recombinant virus (BAV3.502) was plaque-purified on VIDO R2 cells.

The presence of the HE insert was confirmed by Cla I digestion, which indicated the loss of a 12.2 kb fragment characteristic of BAV3.500 and its replacement by a fragment of 14.1 kb. Southern blot analysis with a HE probe confirmed that HE sequences were present in the 14.1 kb fragment.

Example 7

Construction of BAV3.304, a Recombinant BAV with an Insertion of the Green Fluorescent Protein Gene in the E3 Region A green fluorescent protein (GFP) gene, under the control of the cytomegalovirus immediate early promoter and the bovine growth hormone polyadenylation signal, was obtained from the plasmid pQBI 25 (Quantum Biotechnologies) by Bgl II and Dra III digestion followed by treatment with T4 DNA polymerase to generate blunt ends. This fragment was then inserted into the Srf I site of pBAV-301, with the GFP gene in the same transcriptional orientation as E3, to generate pBAV-301.gfp.

pBAV-301 was constructed by ligating a 7,635 base-pair Kpn I-Ssp I fragment of pFBAV302 to Kpn I/Not I digested PpolyIIsnl4. pFBAV302 is a BAV genome with with an E3 deletion in which the deleted E3 sequences are replaced by a Srf I site.

A Kpn I/Sma I fragment of pBAV30t.gfp, encompassing the modified E3 region, was introduced into E. coli BJ 5183, along with Srf I-digested pFBAV.302. In vivo recombination between these two DNA molecules generated pFBAV.304, a BAV genome containing a GFP gene in a deleted E3 region. See FIG. 9.

PacI-digested pFBAV.304 DNA was transfected into VIDO-R2 cells (5–10 µg per 60 mm diameter dish of cell monolayer) using Lipofectin (GIBCO/BRL). After incubation at 37° C., cells showing cytopathic effects were collected and subjected to two cycles of freeze-thawing, and recombinant virus (BAV3.304) was plaque-purified on VIDO R2 cells.

pFBAV.304 viral DNA was analyzed by Bam HI digestion followed by agarose gel electrophoresis. Bam HI digestion of pFBAV.304 produced a 2.3 kb fragment that was not present in the parental BAV.E3d genome. Southern blot analysis with a GFP probe confirmed that GFP sequences were present in the 2.3 kb Bam HI fragment.

Example 8

Abortive Infection of Noncomplementing Cell Lines with E1 Mutant Viruses

FBRC and R2 cells were infected with wild-type or recombinant BAV at a MOI of less than one, cultured for one week, subjected to two freeze-thaw cycles,and titrated on VIDO R2 cells. Wild-type BAV-3, an E3 deletion (BAV-3.E3d) and BAV3.304 grew to high titers (up to $10^9$ pfu/ml) in all cell lines tested, whereas replication-defective recombinant viruses containing deletions in E1 and E3 (BAV3.500, BAV3.501 and BAV3.502) grew only in VIDO R2 cells, generating titers of approximately $10^7$ pfu/ml. See FIG. 10.

Example 9

Kinetics of gD Expression from Recombinant Viruses

Kinetics of gD expression by BAV3.501 (Example 5) were determined, by immunoprecipitation, at three time points after infection of VIDO R2 or MDBK cells (FIG. 11). For immunoprecipitation analysis, confluent monolayers of VIDO R2 cells in six-well dishes were infected with virus at a MOI of greater than 5. Cells were preincubated for 2 h in minimal essential medium lacking methionine and cysteine prior to labeling for 4 h with 50 µCi of [$^{35}$S]methionine (Tran$^{35}$S-label, phosphate-buffered saline, 1,000 Ci/mmol, ICN Radiochemicals, Inc. Irvine, Calif.). The cells were washed with phosphate-buffered saline, harvested by scraping, then lysed with ice-cold modified radioimmuno-precipitation assay buffer. Radiolabeled proteins were immunoprecipitated with a pool of anti-BHV-1 gD monoclonal antibodies (Hughes et al. (1988) Arch. Virol. 103:47–60) and analyzed by SDS-polyacrylamide gel electrophoresis. After running, the gels were dried and labeled protein bands were visualized by autoradiography.

Electrophoretic analysis of metabolically labeled immunoprecipitates from lysates of BAV3.501-infected VIDO R2 cells revealed immunoreactive proteins with molecular weights of approximately 63 kDa and 71 kDa (FIG. 11A, lanes 5 and 6), corresponding to unglycosylated and glycosylated forms of gD, respectively. These molecular weights correspond to those of authentic gD immunoprecipitated from BHV-1-infected cell extracts (FIG. 11A, lane 3). No proteins of corresponding molecular weight were detected in mock-infected cells (FIG. 11A, lane 1) or BAV-3-infected cells (FIG. 11A, lane 2).

In BAV3.501-infected cells, expression of gD was first detected 24 hours after infection (FIG. 11A, lane 5) and it continued to be produced up to 36 hours post-infection (FIG. 11A, lane 6), which was the final time point used in the study. Kinetics of gD expression from BAV3.501 were similar in MDBK cells (FIG. 11B, lanes 5 and 6).

Example 10

Kinetics of HE Expression from Recombinant Viruses

Kinetics of HE expression by BAV3.502 (Example 6) were determined in VIDO R2 cells (FIG. 12). Immunoprecipitation analysis was conducted as described in Example 10, except that rabbit polyclonal anti-BCV antibodies were used for immunoprecipitation. Deregt et al. (1987) Virology 161:410–420; and Deregt et al. (1989) J. Gen. Virol. 70:993–998.

Anti-BCV polyclonal rabbit serum immunoprecipitated a 65 kDa polypeptide from R2 cells infected with BAV3.502 (lanes 5 and 6). This polypeptide comigrated with authentic HE protein produced from BCV-infected cells (lane 3), and no corresponding protein was immunoprecipitated from mock-infected cells (lane 1) or from wild-type BAV-3-infected cells (lane 2). Kinetics of HE expression (lanes 5 and 6) were similar to those observed for gD in BAV3.501-infected cells.

Example 11

Glycosylation of Recombinant gD and HE Proteins

Glycosylation of recombinant gD and HE proteins was examined by immunoprecipitation following labeling of infected cells with [$^3$H]glucosamine. Results of these studies confirmed that the proteins produced by recombinant bovine adenoviruses are glycosylated and are indistinguishable in migration rate (on gels) from the authentic proteins synthesized in virus-infected cells.

Example 12

Expression of GFP in BAV3.304-infected Cells

Lysates of cells infected with BAV3.304 were examined by protein blotting using GFP-specific polyclonal antibodies (Clontech, Palo Alto, Calif.). See FIG. 13. Cell extracts (5 µg per lane) were separated on a 10% polyacrylamide-SDS gel and the gel weas blotted onto a nitrocellulose membrane. Nonspecific binding sites on the membrane were blocked with 1% bovine serum albumin and the blots were incubated with anti-GFP polyclonal antibodies. After antibody binding, the blots were washed and exposed to anti-mouse or anti-rat IgG conjugated to horseradish peroxidase (HRP) or alkaline phosphatase (AP), and developed using HRP or AP development kits (Bio-Rad, Hercules, Calif.).

Anti-GFP serum identified a protein of 28 kDa in BAV3.304-infected cells (lanes 1–3) that was not present in mock-infected (lane 4) or wild-type BAV-S infected cells (lane 5). Recombinant GFP was detected between 12 and 36 hours after infection (lanes 1–3).

Deposit of Biological Materials

The following materials were deposited and are maintained with the American Type Culture Collection, Gaithersburg, Md.

Recombinant Cell Lines

Primary fetal bovine retinal cells transformed with HAd-5 E1 sequences:

| Material | Accession No. | Deposit Date |
|---|---|---|
| VIDO R2 | ATCC PTA-156 | June 1, 1999 |

While the foregoing invention has been described in some detail by way of illustration and example for purposes of clarity of understanding, it will be apparent to those skilled in the art that various changes and modifications may be practiced without departing from the spirit of the invention. Therefore the foregoing descriptions and examples should not be construed as limiting the scope of the invention.

What is claimed is:

1. A recombinant fetal reitna cell of bovine origin that expresses a human E1 adenovirus gene, wherein the cell is permissive for the replication of a replication-defective recombinant bovine adenovirus vector having a mutation in the E1 gene region.

2. The cell of claim 1 comprising human adenovirus E1 nucleotide sequences.

3. The cell of claim 2 wherein the E1 sequences are integrated in the genome of the cell.

4. The cell of claim 2 wherein the human adenovirus is human adenovirus type 5 (HAd-5).

5. The cell of claim 1 wherein the cell is a fetal bovine retina cell.

6. The cell of claim 1, wherein the cell comprises a replication-defective recombinant bovine adenovirus vector having a mutation in the E1 gene region.

7. The cell of claim 6 wherein the mutation is a deletion of part or all of the E1 region.

8. The cell of claim 7, wherein the recombinant bovine adenovirus vector is mutated in the E3 region.

9. The cell of claim 8 wherein said mutation is a deletion of part or all of the E3 region.

10. The cell of claim 6 wherein the recombinant bovine adenovirus vector comprises a heterologous sequence.

11. The cell of claim 10, wherein the heterologous sequence is inserted in the E1 region.

12. The cell of claim 10 wherein said heterologous sequence encodes a determinant of a mammalian pathogen.

13. The cell of claim 12 wherein said pathogen is bacterial.

14. The cell of claim 12 wherein said pathogen is viral.

15. The cell of claim 13 wherein said bacterial pathogen includes Pasteurella sp. or Hemophilus sp.

16. The cell of claim 14 wherein said viral pathogen includes herpesvirus, influenzavirus, parainfluenzavirus, rotavirus, coronavirus, viral diarrhea virus, picornavirus, adenovirus, retrovirus or lentivirus.

17. The cell of claim 10 wherein said heterologous sequence encodes a cytokine.

18. The cell of claim 10 wherein said heterologous sequence encodes a therapeutic polypeptide.

19. A recombinant fetal retina cell of bovine origin that expresses a human adenovirus E1 gene and wherein the cell comprises a replication-defective recombinant bovine adenovirus vector having a deletion in the E1 gene region, wherein said cell is permissive for the growth of said replication-defective bovine adenovirus vector.

20. A method for propagating a recombinant, replication-defective bovine adenovirus wherein said method does not produce recombinant, replication-competent bovine adenovirus, comprising growing a replication-effective bovine adenovirus vector, wherein said vector comprises a mutation in the E1 gene region, in a fetal retina cell of bovine origin that expresses a hu E1 gene and which is permissive for the growth of said replication-defective bovine adenovirus vector.

21. The method of claim 20 wherein said cell is a fetal bovine retina cell.

22. The method of claim 20 wherein said human E1 function is from human adenovirus type 5 (HAd-5).

23. The method of claim 20 wherein said cell comprises human adenovirus E1 nucleotide sequences.

24. The method of claim 23 wherein the E1 sequences are integrated in the genome of the cell.

25. The method of claim 20 wherein said adenovirus vector further comprises a deletion of part or all of the E3 gene region.

26. The method of claim 20 wherein said adenovirus vector comprises a heterologous sequence.

27. The method of claim 26 wherein said heterologous sequence encodes a determinant of a mammalian pathogen.

28. The method of claim 27 wherein said pathogen is bacterial.

29. The method of claim 27 wherein said pathogen is viral.

30. The method of claim 28 wherein said bacterial pathogen includes Pasteurella sp. or Hemophilus sp.

31. The method of claim 29 wherein said viral pathogen includes herpesvirus, influenzavirus, parainfluenzavirus, rotavirus, coronavirus, viral diarrhea virus, picornavirus, adenovirus, retrovirus or lentivirus.

32. The method of claim 26 wherein said heterologous sequence encodes a cytokine.

33. The method of claim 26 wherein said heterologous sequence encodes a therapeutic polypeptide.

* * * * *

UNITED STATES PATENT AND TRADEMARK OFFICE
CERTIFICATE OF CORRECTION

PATENT NO.     : 6,458,586 B1
DATED          : October 1, 2002
INVENTOR(S)    : Suresh K. Tikoo et al.

It is certified that error appears in the above-identified patent and that said Letters Patent is hereby corrected as shown below:

Column 23,
Line 25, please replace "reitna" with -- retina --;
Line 57, please replace "Pasteurella sp." with -- *Pasteurella sp.* --;
Line 57, please replace "Hemophilus sp." with -- *Hemophilus sp.* --;

Column 24,
Line 19, please replace "replication-effective" with -- replication-defective --;
Line 22, please replace "hu" with -- human --;
Line 46, please replace "Pasteurella sp." with -- *Pasteurella sp.* --;
Line 46, please replace "Hemophilus sp." with -- *Hemophilus sp.* --;

Signed and Sealed this

Twenty-fifth Day of February, 2003

JAMES E. ROGAN
*Director of the United States Patent and Trademark Office*